(12) United States Patent
Pan et al.

(10) Patent No.: US 10,510,967 B2
(45) Date of Patent: Dec. 17, 2019

(54) ORGANIC COMPOUND, AND MIXTURE, FORMULATION AND ORGANIC DEVICE COMPRISING THE SAME

(71) Applicant: GUANGZHOU CHINARAY OPTOELECTRONIC MATERIALS LTD., Guangzhou (CN)

(72) Inventors: Junyou Pan, Guangzhou (CN); Hong Huang, Guangzhou (CN)

(*) Notice: Subject to any disclaimer, the term of this patent is extended or adjusted under 35 U.S.C. 154(b) by 58 days.

(21) Appl. No.: 15/535,026

(22) PCT Filed: Dec. 11, 2015

(86) PCT No.: PCT/CN2015/097191
§ 371 (c)(1),
(2) Date: Dec. 11, 2017

(87) PCT Pub. No.: WO2016/091219
PCT Pub. Date: Jun. 16, 2016

(65) Prior Publication Data
US 2018/0130955 A1    May 10, 2018

(30) Foreign Application Priority Data
Dec. 11, 2014    (CN) .......................... 2014 1 0765360

(51) Int. Cl.
| H01L 51/00 | (2006.01) |
| C07F 15/00 | (2006.01) |
| C09K 11/06 | (2006.01) |
| C07D 487/04 | (2006.01) |
| H01L 51/50 | (2006.01) |

(52) U.S. Cl.
CPC ........ *H01L 51/0072* (2013.01); *C07D 487/04* (2013.01); *C09K 11/06* (2013.01); *H01L 51/0071* (2013.01); *C09K 2211/1018* (2013.01); *H01L 51/5012* (2013.01); *H01L 51/5016* (2013.01); *H01L 2251/552* (2013.01)

(58) Field of Classification Search
None
See application file for complete search history.

(56) References Cited

U.S. PATENT DOCUMENTS

| 3,567,450 A | 3/1971 | Brantly et al. |
| 3,615,404 A | 10/1971 | Price et al. |
| 4,720,432 A | 1/1988 | VanSlyke et al. |
| 4,769,292 A | 9/1988 | Tang et al. |
| 5,061,569 A | 10/1991 | VanSlyke et al. |
| 5,121,029 A | 6/1992 | Hosokawa et al. |
| 5,130,603 A | 7/1992 | Tokailin et al. |
| 6,020,078 A | 2/2000 | Chen et al. |
| 6,251,531 B1 | 6/2001 | Enokida et al. |
| 6,824,895 B1 | 11/2004 | Sowinski et al. |
| 6,830,828 B2 | 12/2004 | Thompson et al. |
| 6,835,469 B2 | 12/2004 | Kwong et al. |
| 7,029,766 B2 | 4/2006 | Huo et al. |
| 7,250,532 B2 | 7/2007 | Iwakuma et al. |
| 7,767,317 B2 | 8/2010 | Begley et al. |
| 2001/0053462 A1 | 12/2001 | Mishima |

(Continued)

FOREIGN PATENT DOCUMENTS

| CN | 1583691 A | 2/2005 |
| CN | 102282150 A | 12/2011 |

(Continued)

OTHER PUBLICATIONS

State IP Office of P.R. China; International Search Report for counterpart International Application No. PCT/CN2015/097191 containing International Search Report in English, 6 pgs. (dated Mar. 17, 2016).
State IP Office of P.R. China; Written Opinion for counterpart International Application No. PCT/CN2015/097191, 3 pgs. (dated Mar. 17, 2016).
First Office Action for Chinese Patent Application No. 201580067459. 6, issued by SIPO dated Jun. 21, 2018.

(Continued)

*Primary Examiner* — Katie L. Hammer
(74) *Attorney, Agent, or Firm* — Womble Bond Dickinson (US) LLP

(57) ABSTRACT

An organic compound having the following structural formula is provided:

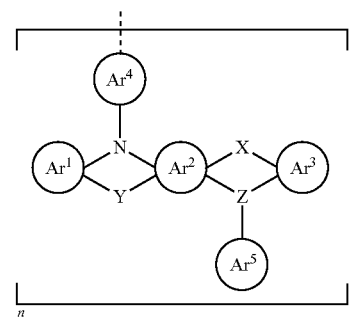

wherein $Ar^1$ to $Ar^5$ are aromatic or heteroaromatic structural units, X, Y, and Z are bridging groups connecting two or three aromatic rings, and n is an integer between 1 and 4. The organic compound has an increased resonance factor and a reduced $\Delta(S1-T1)$, thus facilitating acquisition of thermally-excited delayed fluorescence properties provided with increased light emission efficiency, and implementing high efficiency and extended service life of an OLED component. In addition, a synthesis process for the organic compound is simple and inexpensive. A mixture, a formulation and an organic eletronic device containing the organic compound are also provided.

24 Claims, 1 Drawing Sheet

(56) References Cited

U.S. PATENT DOCUMENTS

| | | |
|---|---|---|
| 2005/0258742 A1 | 11/2005 | Tsai et al. |
| 2006/0210830 A1 | 9/2006 | Funahashi et al. |
| 2006/0222886 A1 | 10/2006 | Kwong et al. |
| 2007/0087219 A1 | 4/2007 | Ren et al. |
| 2007/0252517 A1 | 11/2007 | Owczarczyk et al. |
| 2008/0027220 A1 | 1/2008 | Stossel et al. |
| 2008/0113101 A1 | 5/2008 | Inoue et al. |
| 2009/0061681 A1 | 3/2009 | McMunigal et al. |
| 2009/0134784 A1 | 5/2009 | Lin et al. |
| 2011/0284799 A1 | 11/2011 | Stoessel et al. |
| 2012/0241732 A1* | 9/2012 | Endo ............... C09B 57/00 257/40 |
| 2013/0299743 A1* | 11/2013 | Pan ................. C08G 61/12 252/301.35 |
| 2014/0158992 A1 | 6/2014 | Xia et al. |

FOREIGN PATENT DOCUMENTS

| | | |
|---|---|---|
| CN | 102648268 A | 8/2012 |
| DE | 102005058557 A1 | 6/2007 |
| EP | 1191612 B1 | 3/2002 |
| EP | 1191614 B1 | 3/2002 |
| EP | 1144543 B1 | 3/2004 |
| EP | 1191613 B1 | 3/2006 |
| EP | 1941562 B1 | 7/2008 |
| EP | 1957606 A1 | 8/2008 |
| JP | 2913116 B2 | 6/1999 |
| JP | 2008053397 A | 3/2008 |
| WO | WO2000/070655 A3 | 11/2000 |
| WO | WO01/21729 A1 | 3/2001 |
| WO | WO01/41512 A1 | 6/2001 |
| WO | WO02/002714 A3 | 1/2002 |
| WO | WO02/15645 A1 | 2/2002 |
| WO | WO2005/019373 A2 | 3/2005 |
| WO | WO2005/033244 A1 | 4/2005 |
| WO | WO2006/000388 A1 | 1/2006 |
| WO | WO2006/000389 A1 | 1/2006 |
| WO | WO2006/058737 A1 | 6/2006 |
| WO | WO2006/122630 A1 | 11/2006 |
| WO | WO2007/065549 A1 | 6/2007 |
| WO | WO2007/095118 A2 | 8/2007 |
| WO | WO2007115610 A1 | 10/2007 |
| WO | WO2007140847 A1 | 12/2007 |
| WO | WO2008006449 A1 | 1/2008 |
| WO | WO2009118087 A1 | 10/2009 |
| WO | WO2009146770 A1 | 12/2009 |
| WO | WO2010015307 A1 | 2/2010 |
| WO | WO2010099852 A1 | 2/2010 |
| WO | WO2010031485 A1 | 3/2010 |
| WO | WO2010054728 A1 | 5/2010 |
| WO | WO2010054731 A1 | 5/2010 |
| WO | WO2010086089 A1 | 8/2010 |
| WO | WO2010102709 A1 | 9/2010 |
| WO | WO2010135519 A1 | 11/2010 |
| WO | WO2011110277 A1 | 9/2011 |
| WO | WO2011157339 A1 | 12/2011 |
| WO | WO2012007086 A1 | 1/2012 |
| WO | WO2012007087 A1 | 1/2012 |
| WO | WO2012007088 A1 | 1/2012 |
| WO | WO2012004407 A3 | 6/2012 |
| WO | WO2011141110 A3 | 5/2013 |

OTHER PUBLICATIONS

Search Report for Chinese Patent Application No. 201580067459.6, issued by SIPO dated Jun. 11, 2018.

Newkome et al., "Dendrimers and Dendrons: Concepts, Syntheses, Applications", Weinheim: Wiley-VCH, 2001.

M. A. Baldo et al., "High-efficiency fluorescent organic light-emitting devices using a phosphorescent sensitizer", Nature, vol. 403, Feb. 17, 2000, pp. 750-753.

Adachi et al., "High-efficiency red electrophosphorescence devices", Applied Physics Letters, vol. 78, No. 11, Mar. 12, 2001, pp. 1622-1624.

Kido et al., "Electroluminescence in a Terbium Complex", Chemistry Letters vol. 220, No. 4, Apr. 1990, pp. 657-660.

Johnson et al., "Luminescent Iridium(I), Rhodium(I), and Platinum(II) Dithiolate Complexes", Journal of the American Chemical Society vol. 105, No. 7 , Apr. 1983, pp. 1795-1802.

Kido et al., "Bright red light-emitting organic electroluminescent devices having a europium complex as an emitter", Applied Physics Letters, vol. 65, No. 17, Oct. 24, 1994, pp. 2124-2126.

Wrighton et al., "The Nature of the Lowest Excited State in Tricarbonylchloro-1, 10-phenanthrolinerhenium(I) and Related Complexes", Journal of the American Chemical Society, vol. 96, No. 4, Feb. 20, 1974, pp. 998-1003.

Ma et al., "Electroluminescence from triplet metal—ligand charge-transfer excited state of transition metal complexes", Synthetic Metals vol. 94, Issue 3, May 15, 1998, pp. 245-248.

Helmut Kipphan (Ed.), "Handbook of Print Media: Technologies and Production Methods", Heidelberg: Springer, 2001.

Gu et al., "Transparent light-emitting devices", Nature, vol. 380, 29, Mar. 7, 1996.

Gu et al., "Transparent organic light emitting devices", Applied Physics Letters, vol. 68, No. 19, May 6, 1996, pp. 2606-2608.

Uoyama et al., "Highly efficient organic light-emitting diodes from delayed fluorescence", Nature, vol. 492, Dec. 13, 2012, pp. 234-240.

* cited by examiner

| Material | HOMO | LUMO |
|---|---|---|
| (1) |  | 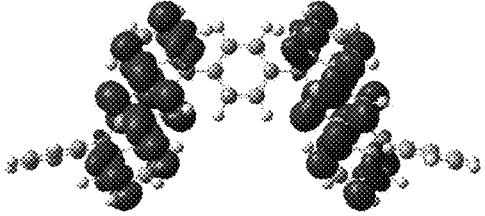 |
| (2) | 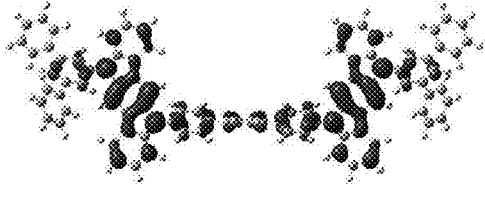 | 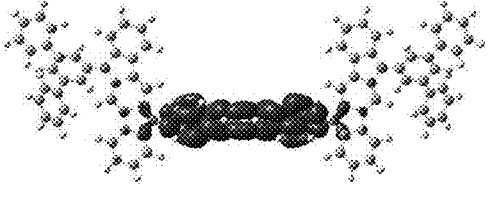 |
| (3) | 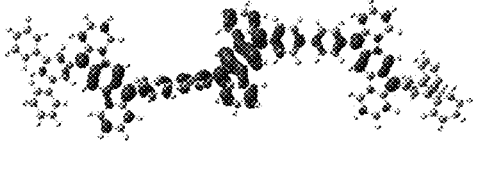 |  |
| (4) | 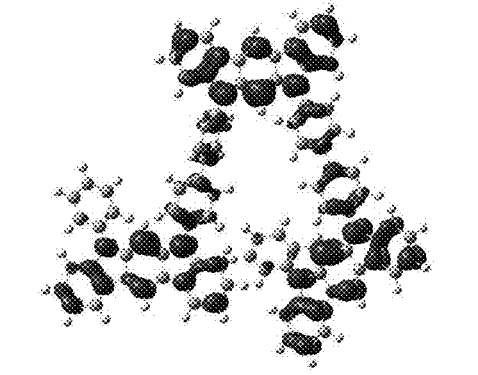 | 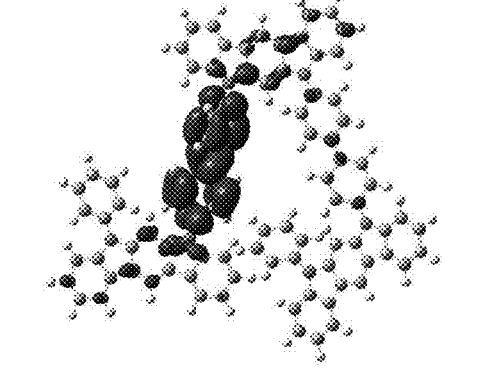 |
| (5) | 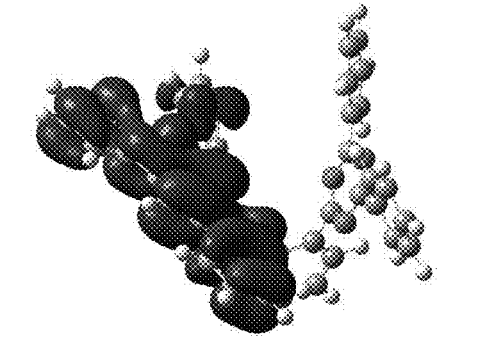 | 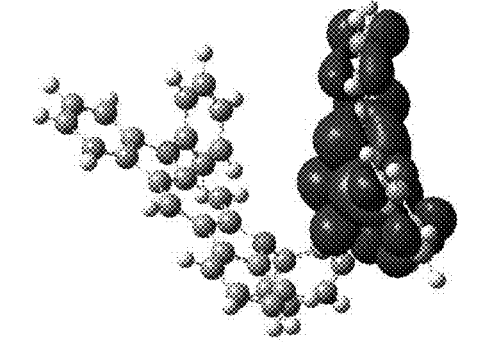 |

ORGANIC COMPOUND, AND MIXTURE, FORMULATION AND ORGANIC DEVICE COMPRISING THE SAME

TECHNICAL FIELD

The present disclosure relates to the field of electroluminescent materials and more particularly to an organic compound with thermal-activated delayed fluorescence, and a mixture, a formulation and an organic electronic device comprising the same.

BACKGROUND

Organic light-emitting diodes (OLEDs) have great potential in implementation of novel optoelectronic devices, such as flat panel displays and lighting applications, because of the synthetic diversity of organic semiconductors, low manufacturing costs, and high-performance optical and electrical properties.

In order to improve the emitting efficiency of organic light-emitting diodes, a variety of material systems based on fluorescent and phosphorescent materials have been developed. The use of fluorescent materials in organic light-emitting diodes has been highly reliable, but its internal electroluminescence quantum efficiency is limited to 25% under the excitation of electric field, because an exciton has a branch ratio of the singlet excited state and triple excited state of 1:3. In contrast, organic light-emitting diodes using phosphorescent materials have achieved almost an internal luminescence quantum efficiency of 100%. However, phosphorescent OLED has a significant problem, the Roll-off effect, that is, luminous efficiency decreases rapidly as the current or brightness increases, which is particularly unfavorable for high-brightness applications.

So far, the phosphorescent material with practical use value is iridium and platinum complexes. Such raw materials are rare and expensive, while the synthesis of complex is complicated, resulting in high costs. In order to overcome problem of rare and expensive raw materials and complicated synthesis of iridium and platinum complexes, Adachi proposed the concept of reverse intersystem crossing so that organic compounds can be used instead of metal complexes to achieve high efficiency comparable with phosphorescent OLEDs. However, most organic compounds with TADF adopt the form of donor groups connected with electron-deficient or electron-acceptor groups, resulting in the complete separation of the highest occupied molecular orbital (HOMO) and the lowest unoccupied molecular orbit (LUMO), which reduces the difference ($\Delta_{ST}$) between the organic compound singlet ($S_1$) and triplet ($T_1$), but also leads to a decrease of the resonance factor (f) of the organic compound and further causes the decrease of the fluorescence quantum efficiency of the organic compound.

In addition, the life of such OLED devices are yet to be improved.

Therefore, the existing technology, especially the solution for the material, needs to be improved and developed.

SUMMARY

In view of the above deficiencies of the prior art, it is an object of the present disclosure to provide an organic compound containing a formulation, an organic electronic device and an application thereof, which is intended to solve the problem that the conventional electroluminescent luminescent material has high cost, fast efficiency decrease under high luminance, and short life, and the problem of low quantum yield of TADF organic luminescent materials.

According to an aspect of the present disclosure, an organic compound is provided, which may comprise a structural unit with the following general structural formula (1), wherein X, Y are doubly-bridging groups, Z is a triply-bridging group, $Ar^1 \sim Ar^5$ represent various aromatic, heteroaromatic, or non-aromatic ring systems.

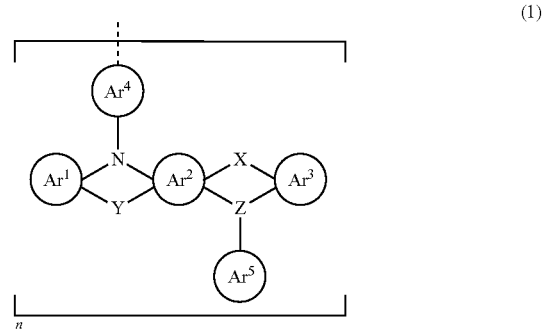

(1)

According to an aspect of the present disclosure, a mixture is also provided, which may comprise an organic compound as described above and at least one organic functional material selected from the group consisting of hole-injection material, hole-transport material, electron-transport material, electron-injection material, electron-blocking material, hole-blocking material, emitter, host material, or a combination thereof.

According to an aspect of the present disclosure, a formulation is also provided, which may comprise an organic compound as described above and at least one organic solvent.

According to an aspect of the present disclosure, also provided is use of an organic compound as described above in an organic electronic device.

According to an aspect of the present disclosure, an organic electronic device comprising the organic compound as described above is provided.

Advantageously, the organic compound of the present disclosure may comprise three aromatic ring or heteroaromatic ring conjugated units having a thermally activated delayed fluorescence luminescence (TADF) characteristic, wherein $(S_1-T_1) \leq 0.30$ eV and the electron cloud distributions of the highest occupied molecular orbital (HOMO) and the lowest unoccupied molecular orbit (LUMO) are fully overlapped, resulting in a relatively high resonant factor (f) in the range of 0.001 to 2.5. The organic compound according to the present disclosure can be used as a TADF luminescent material, which may have improved luminous efficiency and lifetime as an electroluminescent device by cooperating with a suitable host material, providing a solution for light emitting device with low cost, high efficiency, long life and low roll off.

BRIEF DESCRIPTION OF THE DRAWING

FIG. 1 shows the HOMO and LUMO electron cloud distributions of materials (1) to (5).

DETAILED DESCRIPTION OF THE EMBODIMENTS

In one aspect of the present disclosure, there is provided an organic compound and its use in an organic electroluminescent device. The present disclosure will now be described in greater detail with reference to the accompanying drawings so that the purpose, technical solutions, and technical effects thereof are more clear and comprehensible. It is to be understood that the specific embodiments described herein are merely illustrative of, and are not intended to limit, the disclosure.

In one embodiment of the present disclosure, an organic compound having at least one unit with the following general structural formula (1) is provided, wherein the symbols and signs used therein have the following meanings:

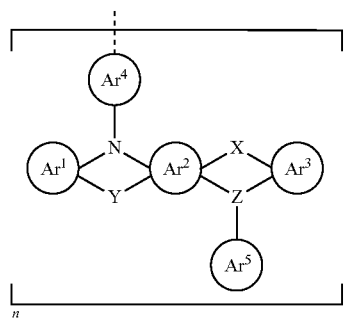

(1)

$Ar^1$, $Ar^2$, $Ar^3$, $Ar^4$ or $Ar^5$ in multiple occurrences may be the same or different and independently selected from the group consisting of an aromatic, heteroaromatic or nonaromatic ring system having 2 to 20 carbon atoms and are optionally substituted with one or more $R^1$ groups, wherein the $R^1$ group in multiple occurrences is the same as or different from each other.

n is 1, or 2, or 3, or 4.

X, Y in each occurrence may be the same or different doubly-bridging group, and they can be connected to $Ar^2$ or $Ar^3$ by a single bond or a double bond and is selected from the group consisting of: a single bond, $N(R^1)$, $B(R^1)$, $C(R^1)_2$, O, C=O, C=S, C=Te, C=NR$^1$, Si(R$^1$)$_2$, C=C(R$^1$)$_2$, S, S=O, SO$_2$, P=O, P=S, P=Se, P=Te, Se, Te, P(R$^1$), and P(=O)R$^1$, or a combination of any two, three or four thereof;

Z in each occurrence is the same or different triply-bridging group, which may be connected to $Ar^1$ or $Ar^2$ or $A^5$ by a single bond or a double bond.

At least one of X and Z is not identical to Y.

$R^1$ in each occurrence may be the same or different and independently selected from the group consisting of —H, —F, —Cl, Br, I, -D, —CN, —NO$_2$, —CF$_3$, B(OR$_2$)$_2$, Si(R$_2$)$_3$, straight chain alkane, alkane ether, alkane sulfide having 1 to 10 carbon atoms, branched alkane, cycloalkane, alkane ether having 3 to 10 carbon atoms; $R^1$ is optionally substituted with one or more active groups $R^2$, and one or more non-adjacent methylene groups of $R^1$ may be optionally replaced by $R^2C=CR^2$, C=C, Si(R$^2$)$_2$, Ge(R$^2$)$_2$, Sn(R$^2$)$_2$, C=O, C=S, C=Se, C=N(R$^2$), O, S, —COO—, or CONR$^2$; one or more H atoms of $R^1$ are optionally replaced by D, F, Cl, Br, I, CN, N$_2$, or replaced by an aromatic amine group containing one or more reactive groups $R^2$ or aromatic group and optionally substituted with a heteroaromatic ring, or replaced by an optionally substituted or unsubstituted carbazole.

$R^2$ in each occurrence may be the same or different and independently selected from H, D, aliphatic alkanes having 1 to 10 carbon atoms, optionally substituted or unsubstituted aryl hydrocarbons, aryl ring or heterocyclic aryl ring containing 5 to 10 carbon atoms.

The dotted line in the general structural formula (1) represents a bond between adjacent monomers in the organic compound.

In a preferred embodiment, $Ar^1$-$Ar^5$ in each occurrence may be the same or different and independently selected from the group consisting of aromatic ring or heteroaromatic ring having 2 to 20 carbon atoms unsubstituted or optionally substituted with $R^1$.

In a compound according to the present disclosure, Z, in each occurrence, may be the same or different and independently selected from a triply-bridging group. In some preferred embodiments, Z may be selected from bridging groups with the following structural formulas:

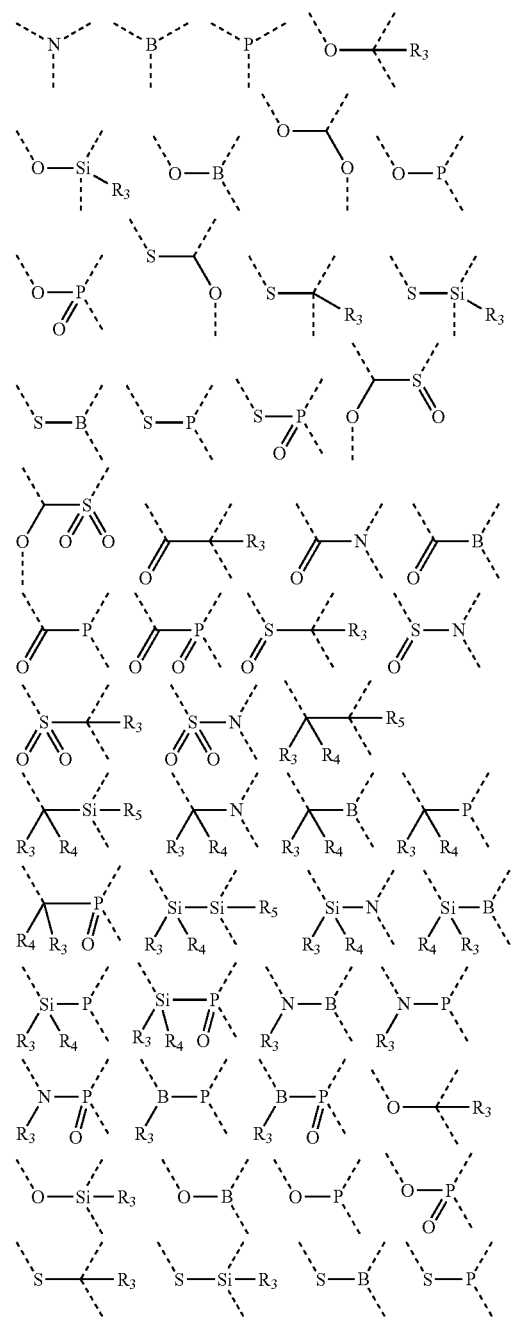

-continued

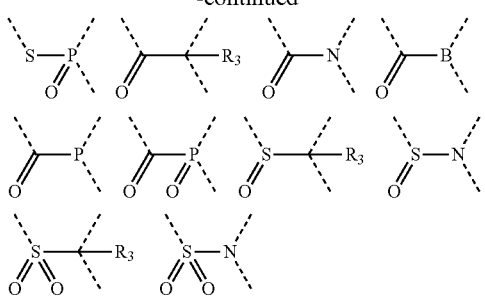

wherein the symbols $R_3$, $R_4$ and $R_5$ may be the same as those defined in claim 1, and the dotted line indicated in the above-mentioned group represents a bond bonded to the structural units $Ar^1$, $Ar^2$, and $Ar^5$.

In the preferred embodiments, the organic compound provided by the present disclosure may include a unit with the following formulas (2), (3), (4), (5) or (6).

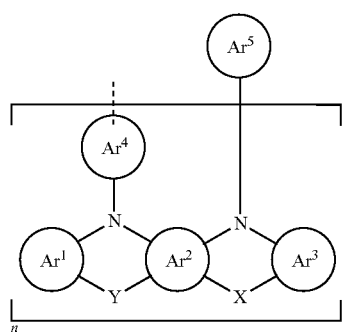

(2)

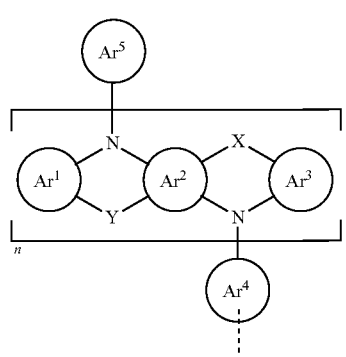

(3)

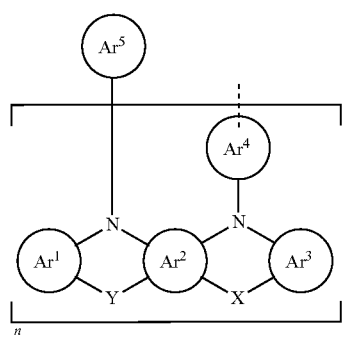

(4)

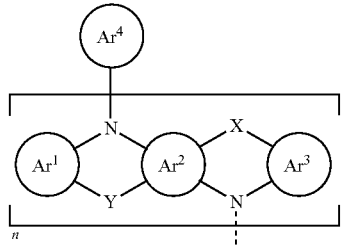

(5)

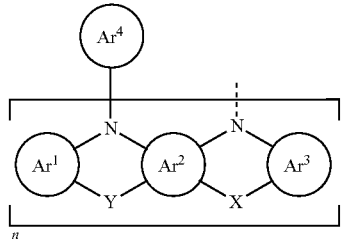

(6)

wherein n may be 1, or 2, or 3 or 4, X or Y in each occurrence may be the same or different bridging group and may be independently selected from a single bond, $N(R^1)$, $B(R^1)$, $C(R^1)_2$, O, $Si(R^1)_2$, $C=C(R^1)_2$, S, S=O, $SO_2$, $P(R^1)$, and $P(=O)R^1$; and a dotted line represents a covalent bond for connection between two groups. All other symbols have the same meaning as defined in the above general formula (1).

Although obvious from the specification, it should be noted once again that the structural elements of the general formulas (2), (3), (4), (5) and (6) herein may be asymmetric substitutions, i.e. different substituents may be present in one unit, or may be present in the bridging groups X, Y. They may, if present, be different or may only appear on one side. Of course, in many occasions it is possible that X or Y may appear as a single bond.

For the purposes of the present disclosure, the aromatic ring system may comprise from 5 to 10 carbon atoms in the ring system, and the heteroaromatic ring system may comprise from 1 to 10 carbon atoms and at least one heteroatom in the ring system, provided that the total number of the carbon atoms and the heteroatoms is at least 4. The heteroatoms may be preferably selected from Si, N, P, O, S and/or Ge, particularly preferably from Si, N, P, O and/or S. For the purposes of the present disclosure, the aromatic or heteroaromatic ring system may not only include aromatic or heteroaromatic groups, but also have a plurality of aryl or heteroaryl groups spaced by short nonaromatic units (<10% of non-H atoms and preferably <5% of non-H atoms, such as C, N or O atoms). Thus, a system such as 9,9'-spirobifluorene, 9,9-diarylfluorene, triarylamine and diaryl ether can be considered to be aromatic ring systems for the purpose of this disclosure.

For the purposes of the present disclosure, non-aromatic ring system may comprise from 1 to 10, preferably from 1 to 3, carbon atoms in the ring system, and may include not only saturated but also partially unsaturated cyclic systems which may be unsubstituted or optionally substituted with one or more $R^1$ groups. $R^1$ may be the same or different in each occurrence and may also comprise one or more heteroatoms, preferably Si, N, P, O, S and/or Ge, and particularly preferably from Si, N, P, O and/or S. Such, for example, may be, but are not limited to, cyclohexyl-like or piperidinelike systems, and may also be cyclooctadiene-like ring systems. These terms are equally applicable to fused non-aromatic ring systems.

For the purposes of the present disclosure, the H atom or bridging group $CH_2$ group on NH may be optionally substituted with an $R^1$ group, wherein $R^1$ may be selected from (1) C1 to C10 alkyl groups, particularly preferably the following groups: methyl, ethyl, n-propyl, isopropyl, cyclopropyl, n-butyl, isobutyl, sec-butyl, t-butyl, cyclobutyl, 2-methylbutyl, n-hexyl, cyclohexyl, n-heptyl, cycloheptyl, n-octyl, cyclooctyl, 2-ethylhexyl, trifluoromethyl, pentafluoromethyl, 2,2,2-trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, and octynyl; (2) a C1 to C10 alkoxy group, particularly preferably methoxy, ethoxy, n-propoxy, isopropoxy, n-butoxy, isobutoxy, sec-butoxy, tert-butoxy or 2-methylbutoxy; (3) C2 to C10 aryl or heteroaryl, which may be monovalent or divalent depending on the application, and in each case can also be optionally substituted with the group $R^1$ mentioned above and may be attached to an aromatic or heteroaromatic ring at any desired position, particularly preferably selected from the following: benzene, naphthalene, anthracene, dinaphthalene, dihydronaphthalene, chrysene, pyrene, fluoranthene, naphthacene, pentacene, benzopyrene, furan, benzofuran, isobenzofuran, dibenzofuran, thiophene, benzothiophene, isobenzothiophene, thiofluorene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenimidazole, pyridimidazole, pyrazine-imidazole, quinoxaline-imidazole, oxazole, benzoxazole, naphthoxazole, anthracenazole, phenoxazole, isoxazole, 1,2-thiazole, 1,3-thiazole, benzothiazole, pyridazine, benzopyridazine, pyrimidine, benzopyrimidine, quinoxaline, pyrazine, phenazine, 1,5-naphthyridine, carbazole, benzocholine, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole. For the purposes of the present disclosure, aromatic and heteroaromatic ring systems are particularly considered to, in addition to the above-mentioned aryl and heteroaryl groups, also refer to Biphenylene, terphenylene, fluorene, spirofluorene, dihydrophenanthrene, tetrahydropyrene, and cis- or trans-indenofluorene.

The compounds of formulas (2), (3), (4), (5) and (6) are preferred, wherein the groups X and Y may form a direct bond with adjacent structural units, i.e., a single bond; or, the X and Y groups may be aromatic or heteroaromatic units unsubstituted or optionally substituted with aromatic or heteroaromatic units at each occurrence by the same or different $R^1$, and connected with the aromatic or heteroaromatic units via mono- and/or di- and/or triple bonds, particularly preferably via directly connection and double bonds.

In addition, the compounds of the general formulas (2), (3), (4), (5) and (6) are preferred, wherein the symbols $Ar^1$ to $A^3$ are the same or different and in each occurrence represents an aromatic heteroaromatic or non-aromatic ring systems having 2 to 10 carbon atoms, which may be unsubstituted or optionally substituted with one or two $R^1$ groups. Preferred aryl or heteroaryl is selected from benzene, naphthalene, anthracene, phenanthrene, pyridine, dinaphthalene or thiophene.

In another preferred embodiment, $Ar^1$ to $A^3$ may comprise the following structural formulas, each of which may be optionally substituted with one or two groups $R^1$.

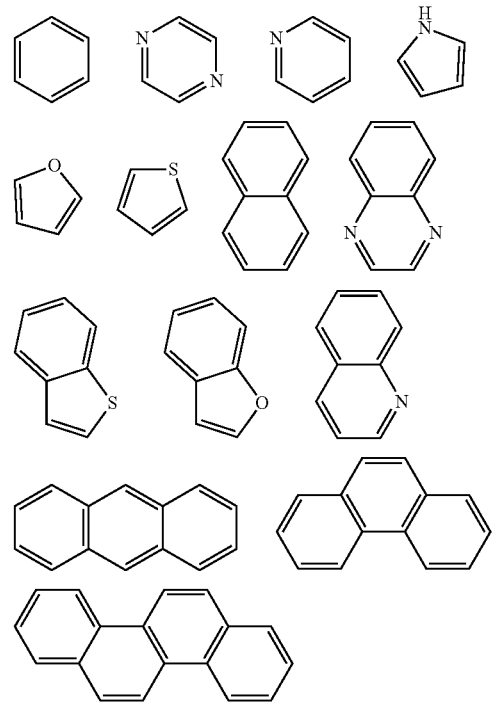

For the purposes of the present disclosure, in a particularly preferred embodiment, $Ar^1$ to $Ar^3$ are all phenyl groups in compounds of the general formulas (2), (3), (4), (5) and (6) which may have the following general formula:

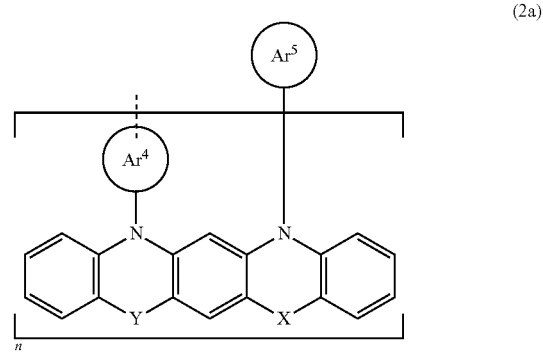

(2a)

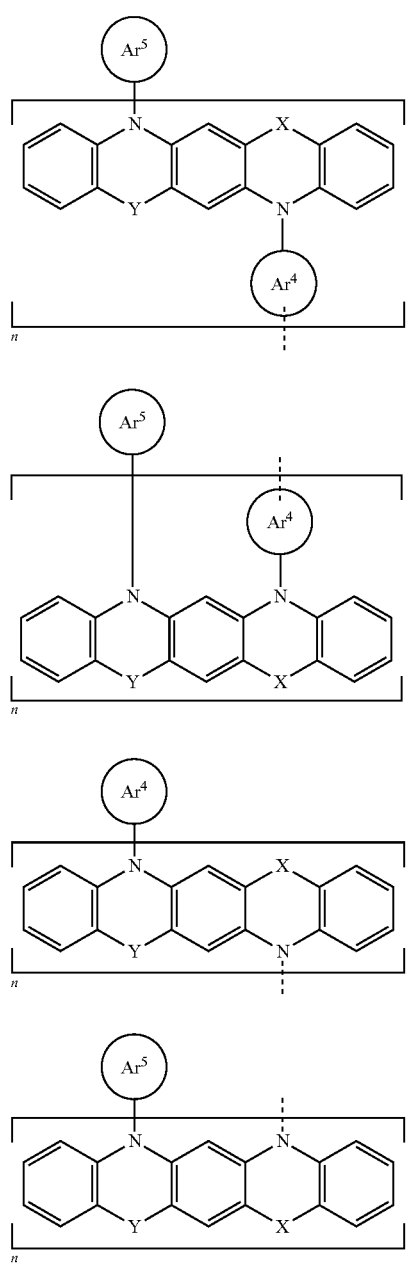
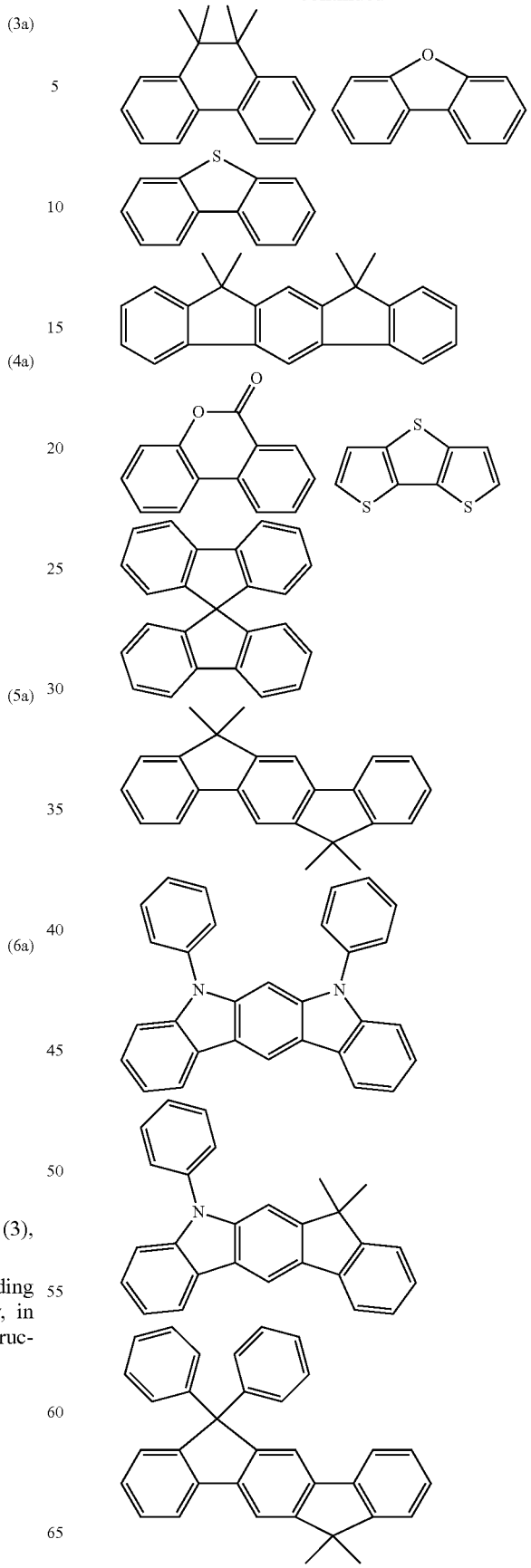
wherein the symbols are as defined for formula (2), (3), (4), (5), (6).
In some preferred embodiments, the compound according to the formula 1 is provided, wherein $Ar^4$, $Ar^5$ may, in multiple occurrences, comprise the same or different structural units below or combinations thereof:
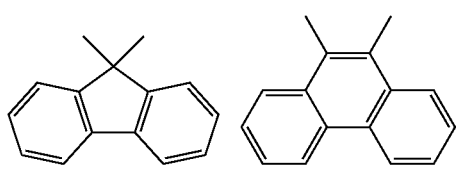

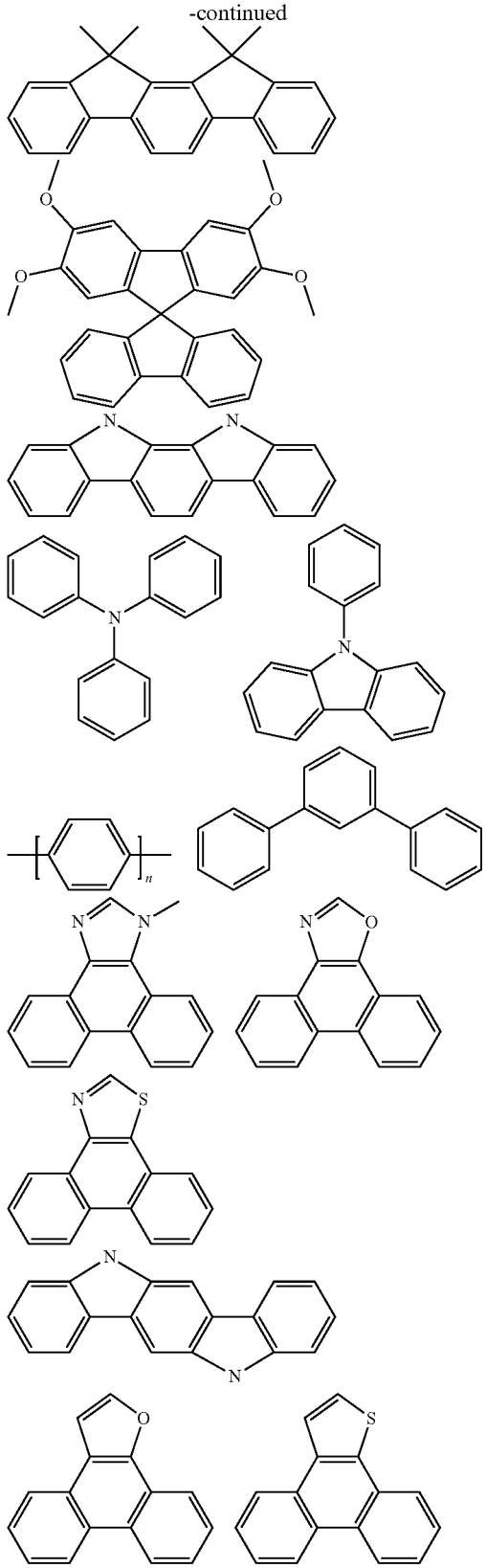

where n is 1 or 2 or 3 or 4.

The compounds according to the present disclosure facilitates the thermally activated delayed fluorescence TADF characteristics. The triplet exciton of the organic compound may be converted to singlet exciton via reverse internal conversion if $(S_1-T_1)$ of the organic compound is sufficiently small, according to the principle of thermally activated delayed fluorescence TADF material (see Adachi et al., Nature Vol 492, 234, (2012)), so as to achieve efficient light emitting. In general, the TADF material is derived from connecting an electron-donor group with an electron-deficient or electron-acceptor group, i.e., having a distinct D-A structure.

In a preferred embodiment, the compound according to the disclosure may have a $(S_1-T_1) \leq 0.30$ eV, more preferably $\leq 0.25$ eV, even more preferably $\leq 0.20$ eV, and most preferably $\leq 0.10$ eV.

In a particularly preferred embodiment, the compounds according to the present disclosure may have no distinct D-A structure, and their HOMO, LUMO tracks may be at least partially overlapping, more preferably largely overlap, and most preferably completely overlapping.

In some embodiments, the compounds of the general formula 1 is provided, in multiple occurrences of $Ar^4$ and $Ar^5$, at least one of the $Ar^4$ and $Ar^5$ groups comprises an electron-donor group and/or at least one of the $Ar^4$ and $Ar^5$ groups comprises an electron-acceptor group.

In a preferred embodiment, the electron-donor group may comprise the following groups:

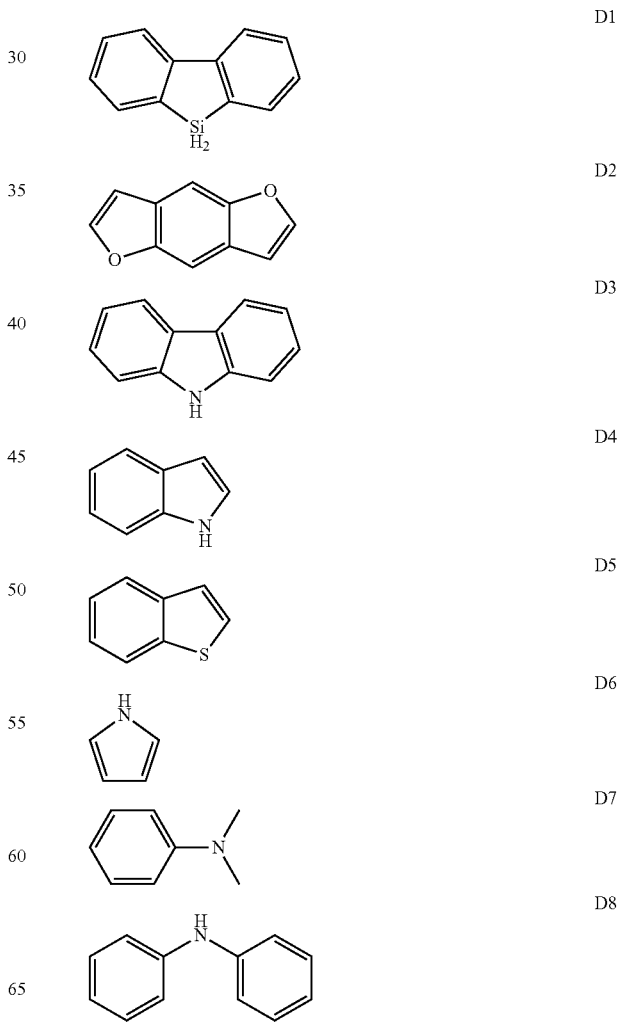

-continued

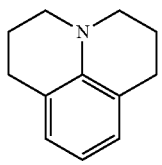
D9

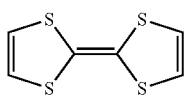
D10

In a preferred embodiment, the electron-acceptor group may be selected from F, cyano group, or a structural unit selected from structural units containing any of the following groups:

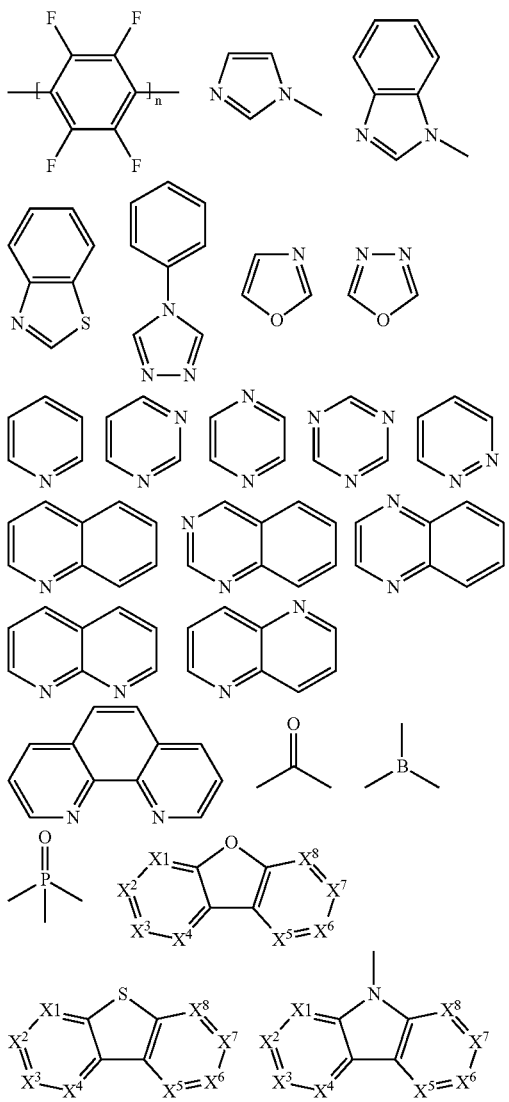

wherein n may be an integer selected from 1 to 3; $X^1$-$X^8$ may be selected from $CR^1$ or N and at least one thereof maybe N; and $R^1$ may be selected from the group consisting of: hydrogen, alkyl, alkoxy, amino, alkene, alkyne, aralkyl, heteroalkyl, aryl and heteroaryl.

As used herein, the term "small-molecule" refers to a molecule that is not a polymer, oligomer, dendrimer, or blend. In particular, there is no repetitive structure in small-molecules. The molecular weight of the small-molecule is no greater than 4000 g/mole, more preferably no greater than 3000 g/mole, and most preferably no greater than 2000 g/mole.

As used herein, the term "polymer" includes homopolymer, copolymer, and block copolymer. In addition, in the present disclosure, the polymer also includes dendrimer. The synthesis and application of dendrimers are described in Dendrimers and Dendrons, Wiley-VCH Verlag GmbH & Co. KGaA, 2002, Ed. George R. Newkome, Charles N. Moorefield, Fritz Vogtle.

The term "conjugated polymer" as defined herein is a polymer whose backbone is predominantly composed of the sp2 hybrid orbital of carbon (C) atom. Some known non-limiting examples are: polyacetylene and poly (phenylene vinylene), on the backbone of which the C atom can also be optionally substituted by other non-C atoms, and which is still considered to be a conjugated polymer when the sp2 hybridization on the backbone is interrupted by some natural defects. In addition, the conjugated polymer in the present disclosure may also comprise aryl amine, aryl phosphine and other heteroarmotics, organometallic complexes, and the like.

The compounds according to the disclosure are small-molecule materials having a molecular weight of ≤4000 g/mol, more preferably ≤3000 g/mol, even more preferably ≤2500 g/mol, and most preferably ≤2000 g/mol.

In particular, the solubility of the organic small-molecule compound can be ensured by having the substituent $R^1$ on the units of the general formulas (2a), (3a), (4a), (5a), (6a) and optionally on the other units. Other substituents, if present, may also promote solubility.

Depending on the type of substitution, the structural units of the general formulas (2a), (3a), (4a), (5a) and (6a) may be suitable for a wide variety of functions in organic small-molecule compounds. Therefore, they are preferably used as the main skeleton of the small-molecule compound or as an emitter. In particular, the substituents X and Y define compounds that are particularly suitable for certain functions. The substituents $R^1$ have an influence on the electronic properties of the units of the general formulas (2a), (3a), (4a), (5a) and (6a).

Examples of preferred units of the general formulas (2a), (3a), (4a), (5a) and (6a) may be the following structures, but are not limited thereto, wherein the bonds in the small-molecule compounds are, in their respective cases, represented by dot-lined bonds. These structures may be optionally substituted at all possible positions. However, for the sake of clarity, possible substituents are not shown.

(7)

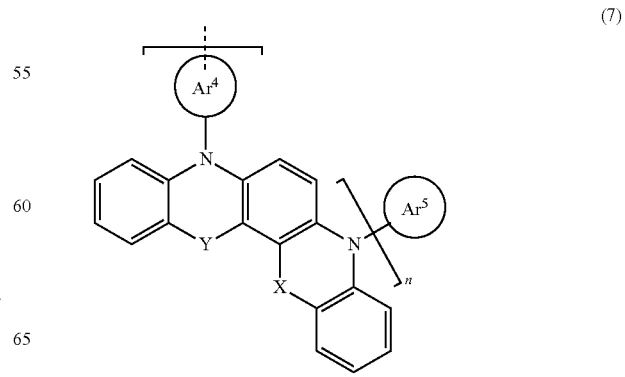

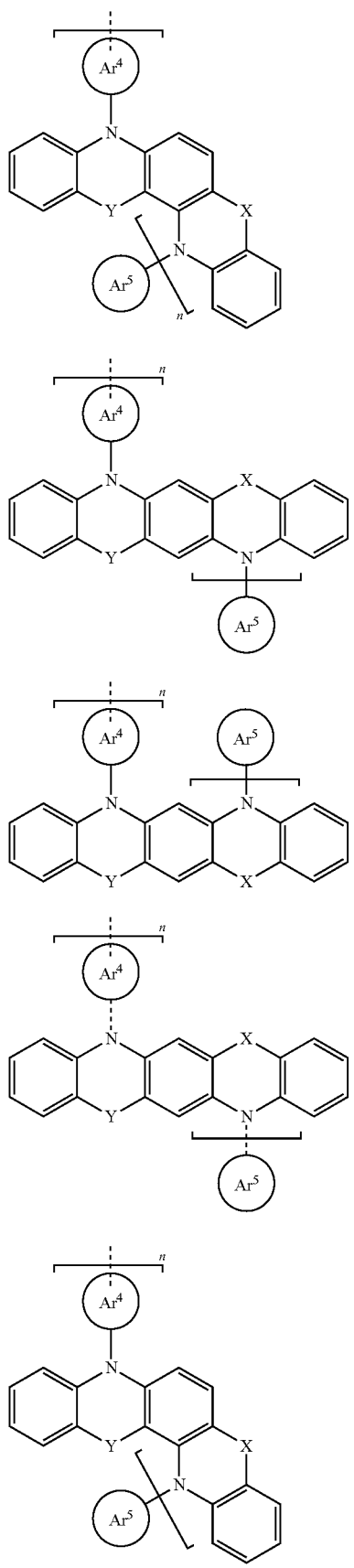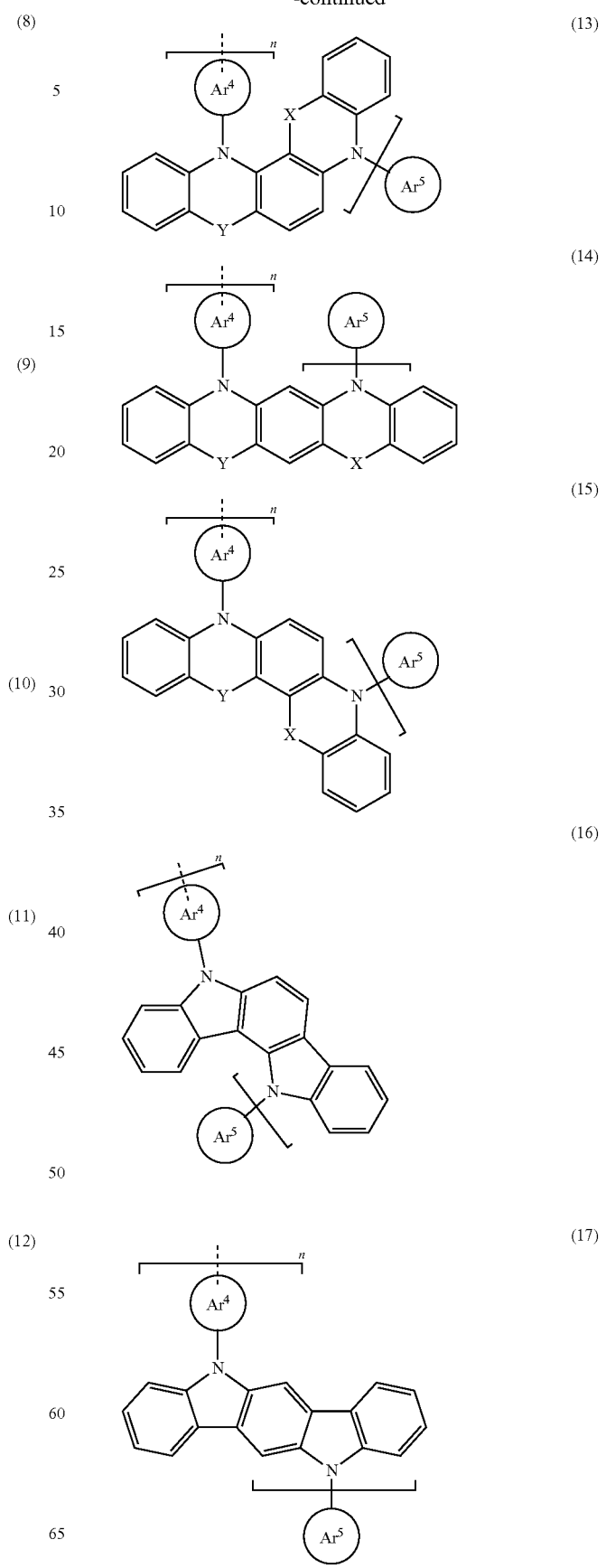

-continued
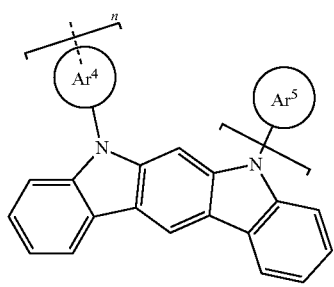
(18)
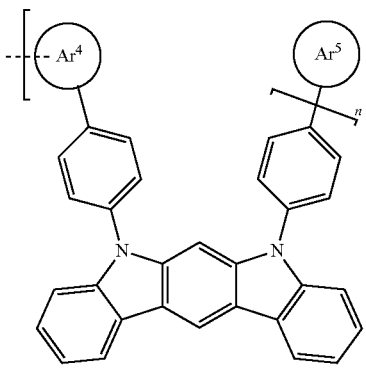
(22)
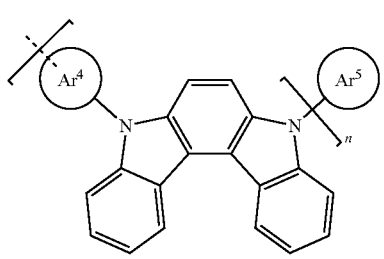
(19)
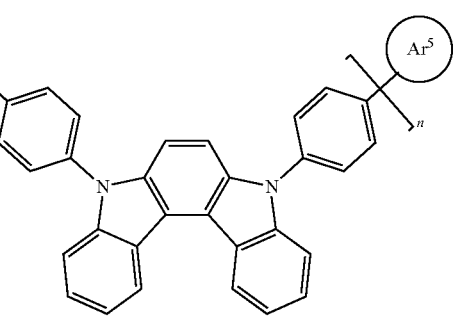
(23)
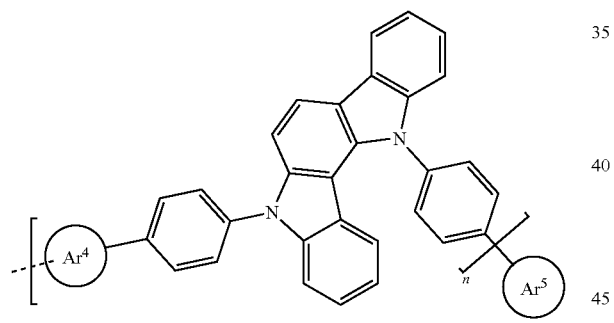
(20)
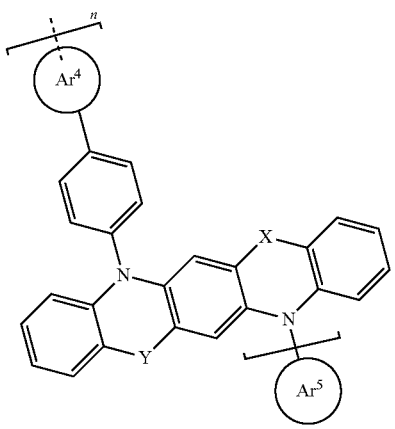
(24)
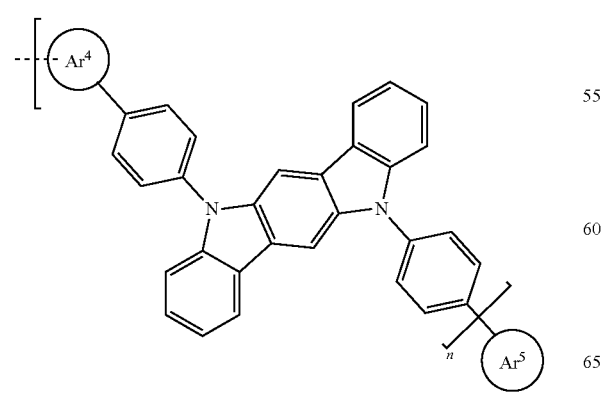
(21)
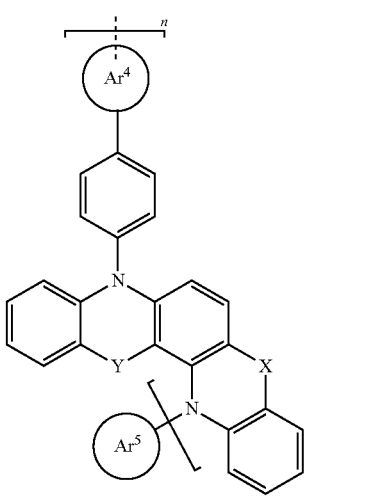
(25)

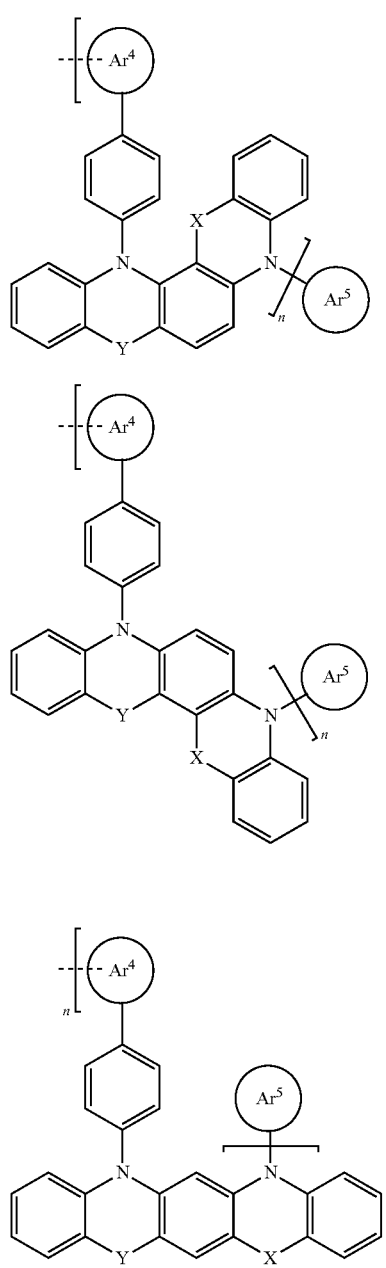
(26)
(27)
(28)
(29)
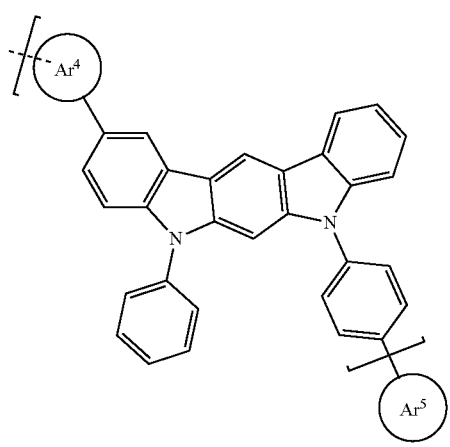
(30)
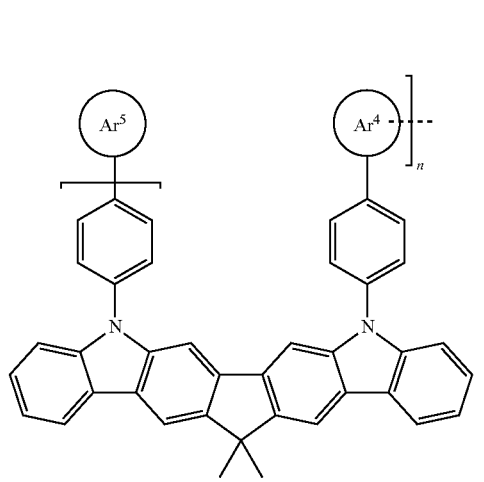
(31)
(32)

-continued
(33)
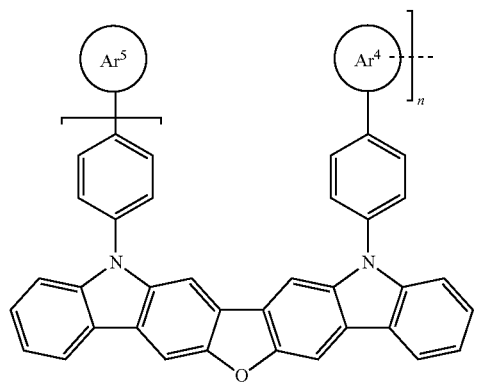
(34)
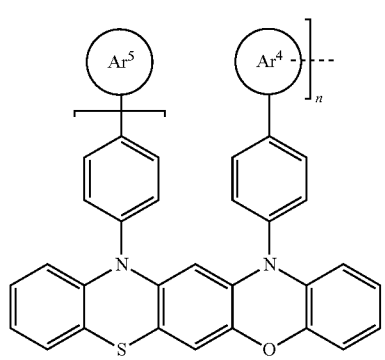
(35)
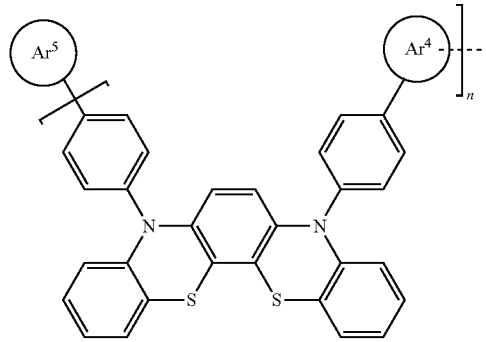
(36)
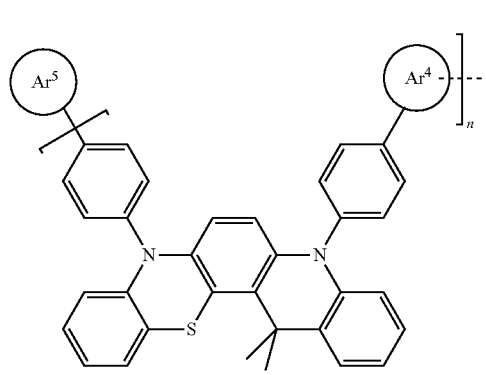
-continued
(37)
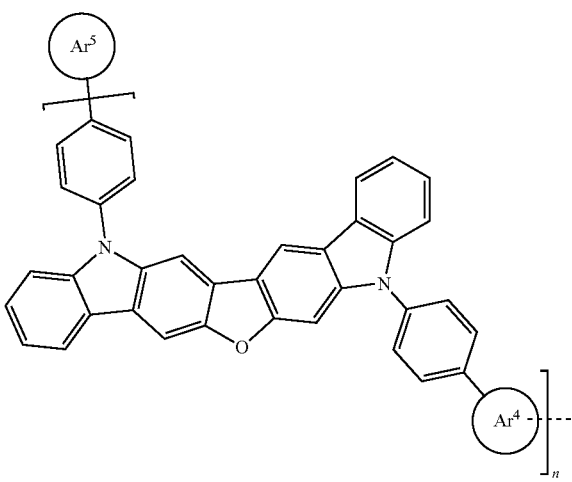
(38)
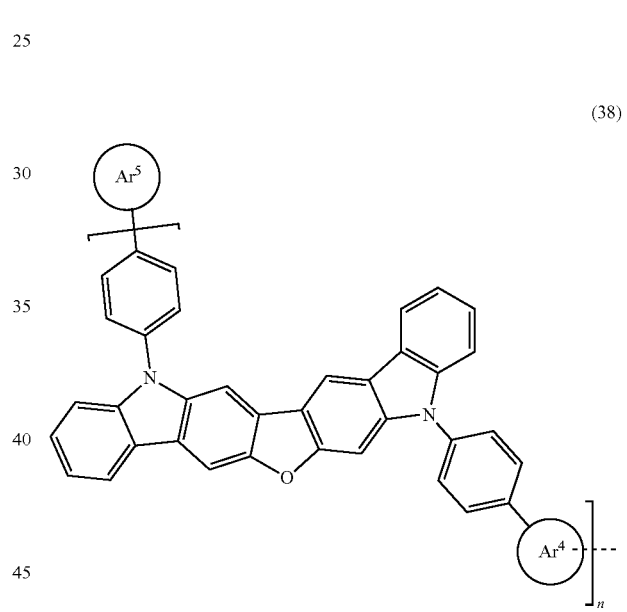
(39)
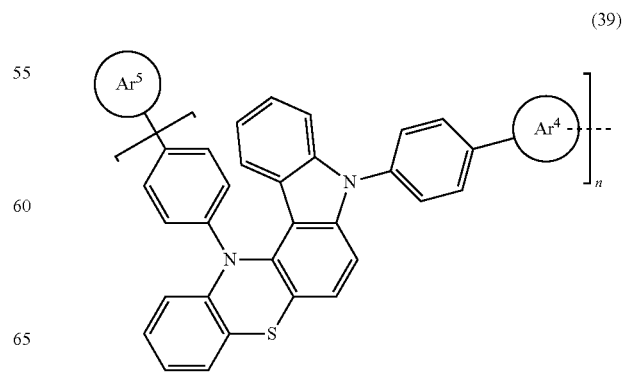

(40)
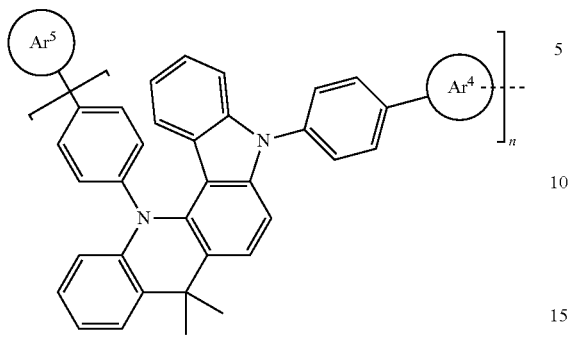
(41)
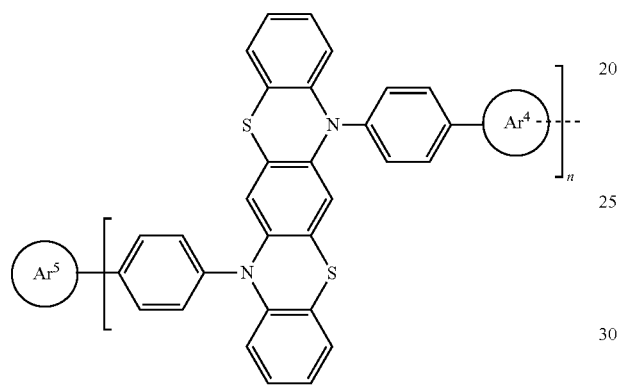
(42)
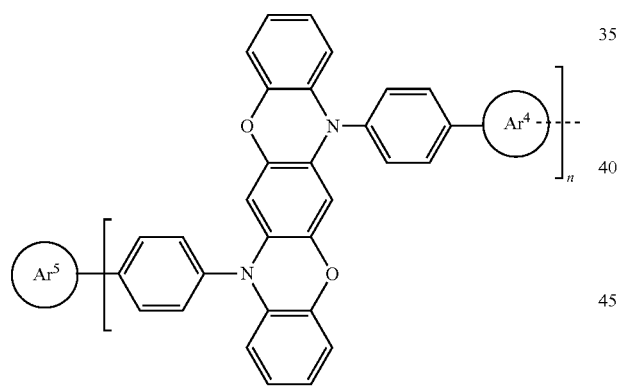
(43)
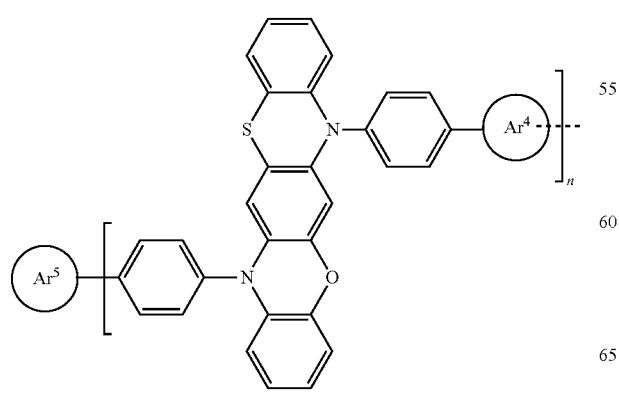
(44)
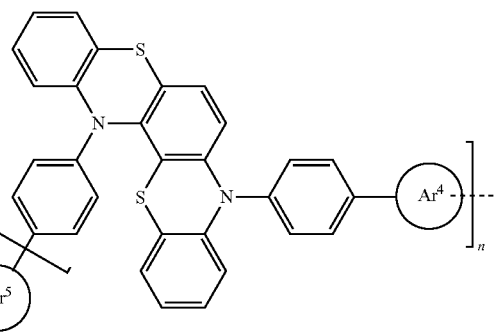
(45)
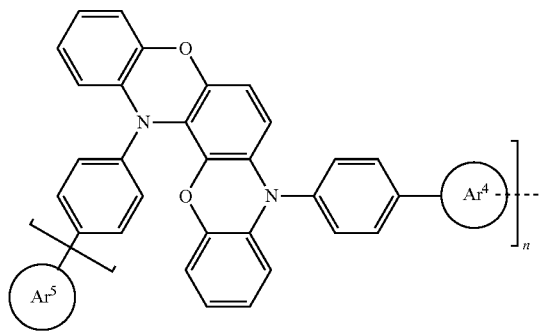
(46)
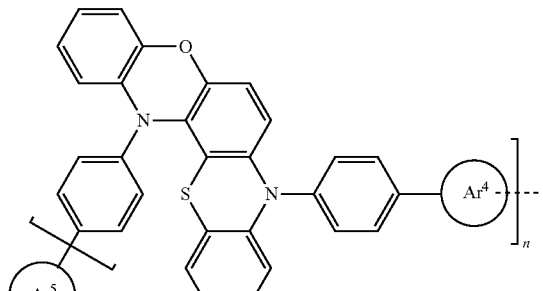
(47)
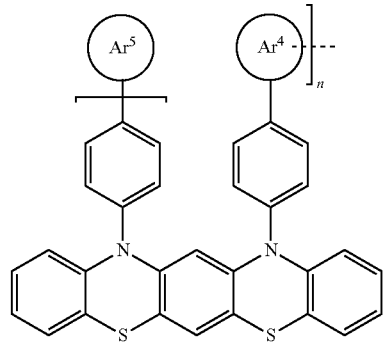

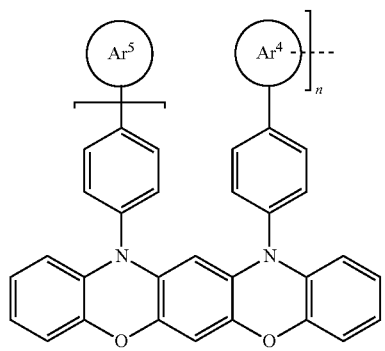
(48)
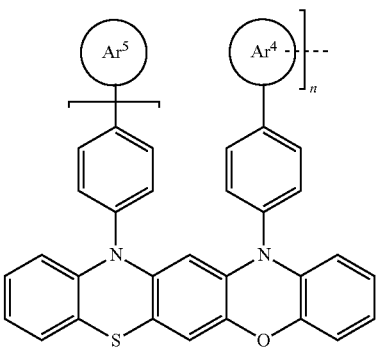
(52)
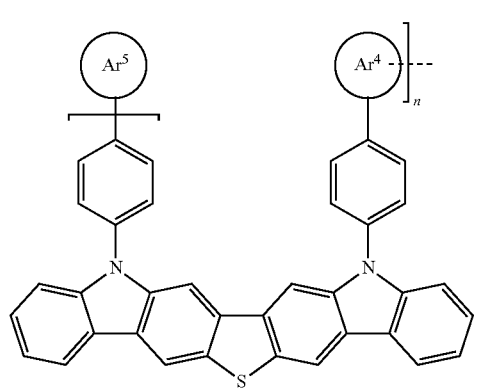
(49)
(53)
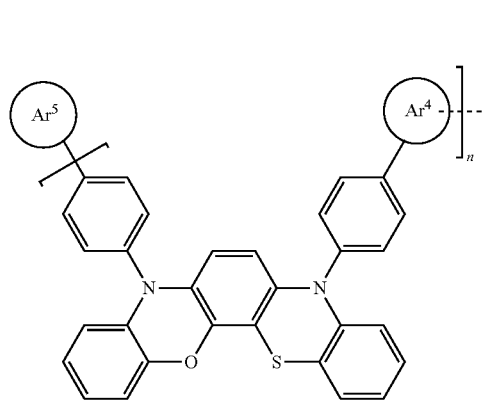
(50)
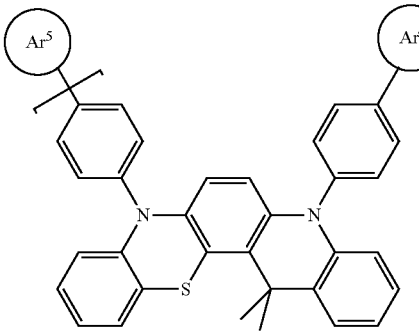
(54)
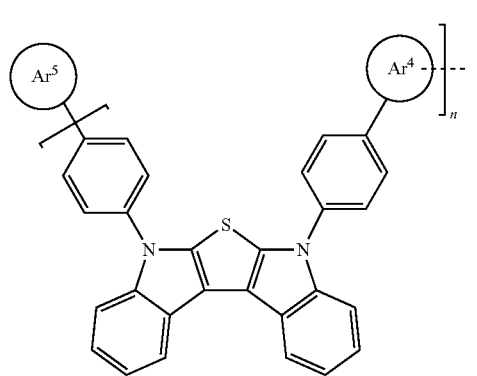
(51)
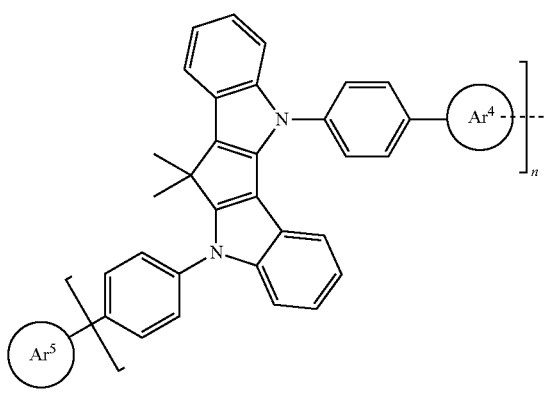
(55)

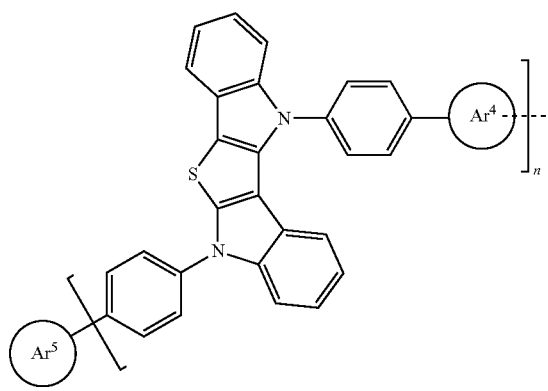
(56)

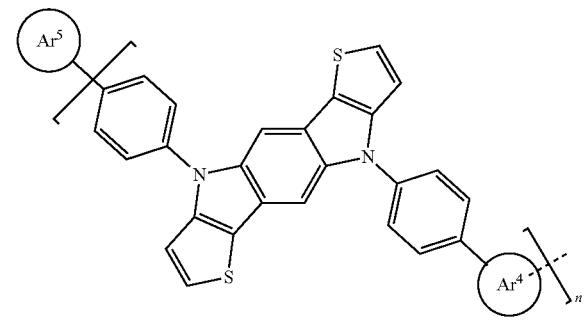
(59)

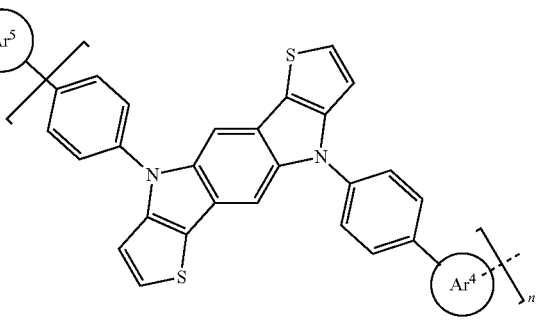
(60)

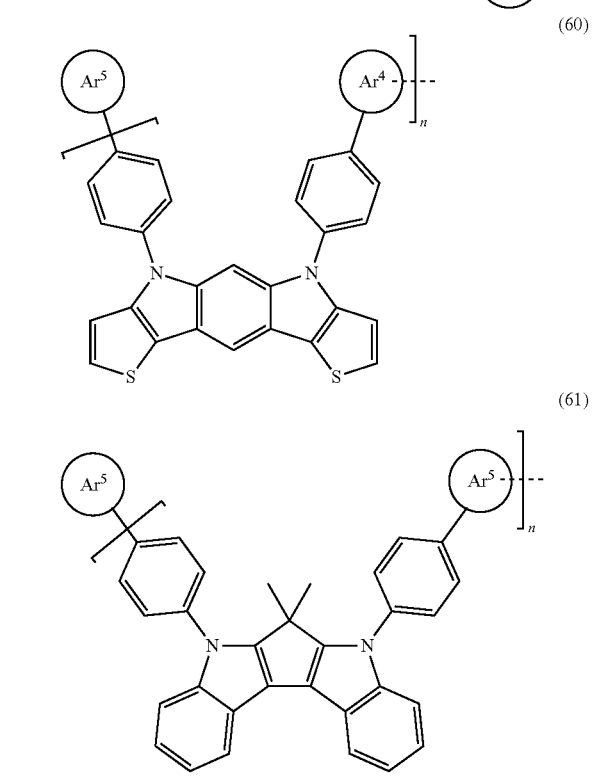
(61)

(57)

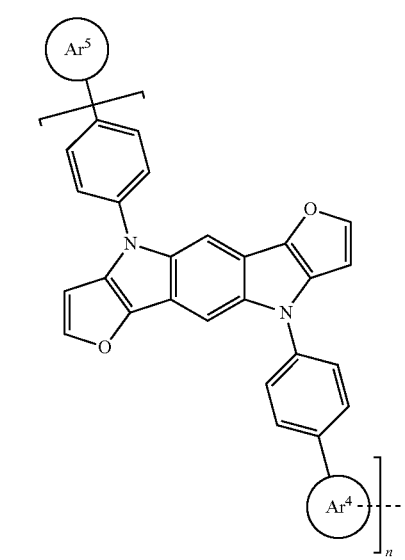

(58)

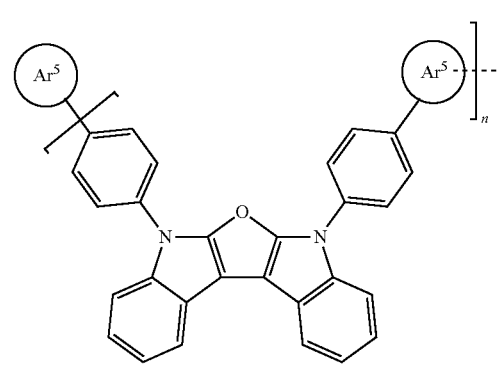
(62)

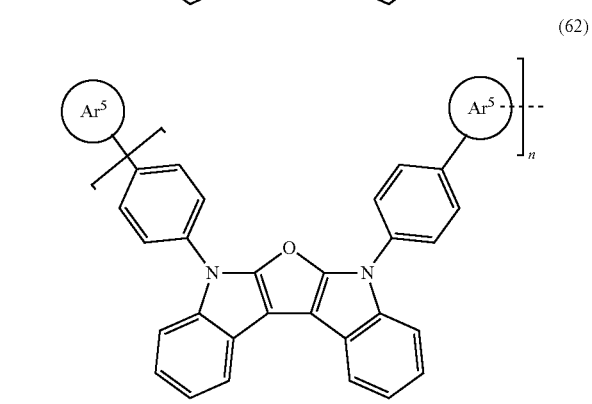

wherein the symbols n, X, Y as well as $A^4$ and $Ar^5$ represent the same meaning as previously described.

The present disclosure also provides a mixture which may comprise, for example, one of the above-mentioned organic compounds, and may comprise at least another organic functional material. The organic functional materials may be selected from HIM, HTM, ETM, EIM, EBM, HBM, Emitter, Host, and the like. The following is a more detailed description the organic functional material (but not limited thereto).

1. HIM/HTM
1. HIM/HTM

The HTM used in the compounds of the present disclosure is also sometimes referred to as a p-type organic semiconductor material. Suitable organic HIM/HTM materials may include any one of the compounds having the following structural units: phthalocyanines, porphyrins, amines, aryl amines, biphenyl triaryl amines, thiophenes, thiophenes such as dithiophenethiophene and thiophthene, pyrrole, aniline, carbazole, indeno-fluorene, and derivatives thereof. Other suitable HIMs also include: fluorocarbon-containing polymers; polymers comprising conductive dopants; conductive polymers such as PEDOT/PSS; self-assembled monomers such as compounds comprising phosphonic acid and sliane derivatives; metal oxides, such as MoOx; metal complex, and a crosslinking compound, or a combination thereof.

In the circumstances of the present disclosure, examples of cyclic aryl amine-derived compounds that can be used as HIM or HTM include, but are not limited to, any of the flowing general structures:

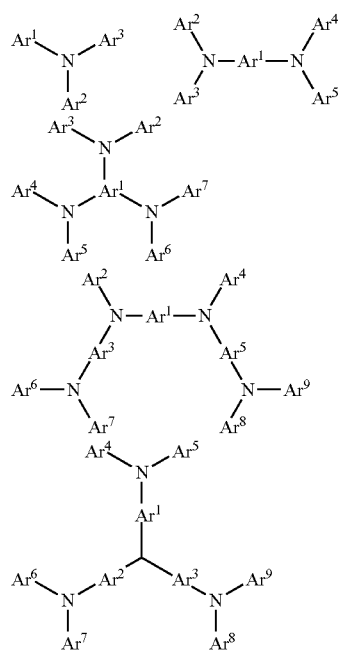

wherein each of $Ar^1$ to $A^9$ may be independently selected from: cyclic aryl groups such as benzene, biphenyl, triphenyl, benzo, naphthalene, anthracene, phenalene, phenanthrene, fluorene, pyrene, chrysene, perylene, azulene; and heterocyclic aryl groups such as dibenzothiophene, dibenzofuran, furan, thiophene, benzofuran, benzothiophene, benzoselenophene, carbazole, pyrazole, imidazole, triazole, isoxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, benzisoxazole, benzothiazole, quinoline, isoquinoline, cinnoline, quinazoline, quinoxaline, naphthalene, phthalein, pteridine, xanthene, acridine, phenazine, phenothiazine, phenoxazine, dibenzoselenophene, benzoselenophene, benzofuropyridine, indolocarbazole, pyridylindole, pyrrolodipyridine, furodipyridine, benzothienopyridine, thienodipyridine, benzoselenophenopyridine, and selenophenodipyridine; groups comprising 2 to 10 ring structures which may be the same or different types of cyclic aryl or heterocyclic aryl and are bonded to each other directly or through at least one of the following groups, for example: oxygen atom, nitrogen atom, sulfur atom, silicon atom, phosphorus atom, boron atom, chain structure unit, and aliphatic cyclic group; and wherein each Ar may be further optionally substituted, and the substituents may optionally be hydrogen, alkyl, alkoxy, amino, alkene, alkyne, aralkyl, heteroalkyl, aryl and heteroaryl.

In one aspect, $Ar^1$ to $Ar^9$ may be independently selected from the group consisting of:

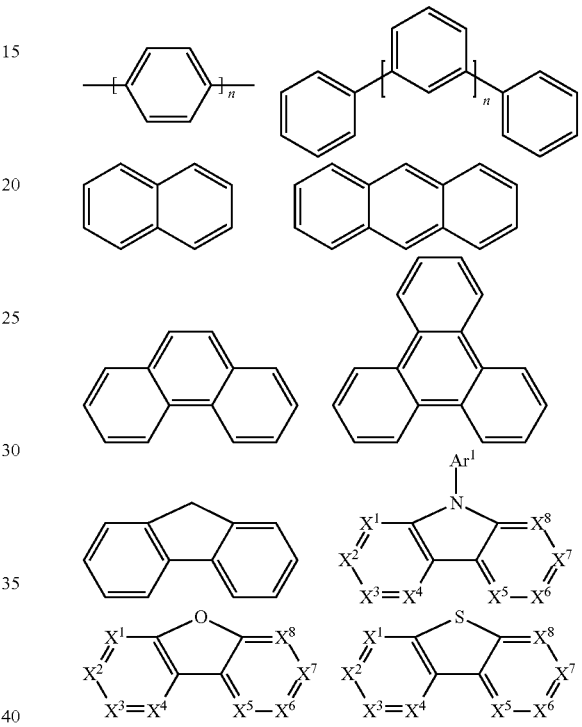

wherein n is an integer of 1 to 20; $X^1$ to $X^8$ are CH or N; $Ar^1$ is as defined above. Additional non-limiting examples of cyclic aryl amine-derived compounds may be found in U.S. Pat. Nos. 3,567,450, 4,720,432, 5,061,569, 3,615,404, and 5,061,569.

Non-limiting examples of metal complexes that may be used as HTM or HIM include, but are not limited to, the general structure as follows:

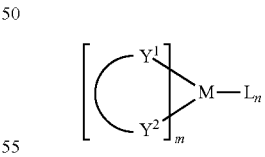

M may be metal having an atomic weight greater than 40; $(Y^1-Y^2)$ is a bidentate ligand, wherein $Y^1$ and $Y^2$ are independently selected from C, N, O, P, and S; L is an auxiliary ligand; m is an integer from 1 to the maximum coordination number of the metal; m+n is the maximum coordination number of the metal. In one embodiment, $(Y^1-Y^2)$ may be a 2-phenylpyridine derivative. In another embodiment, $(Y^1-Y^2)$ may be a carbene ligand. In another embodiment, M may be selected from Ir, Pt, Os, and Zn. In another aspect, the HOMO of the metal complex is greater than −5.5 eV (relative to the vacuum level).

Suitable non-limiting examples of HTM compounds are set forth in the following table:
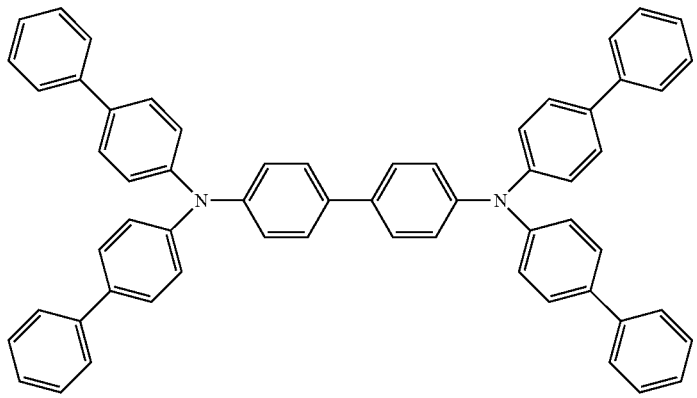
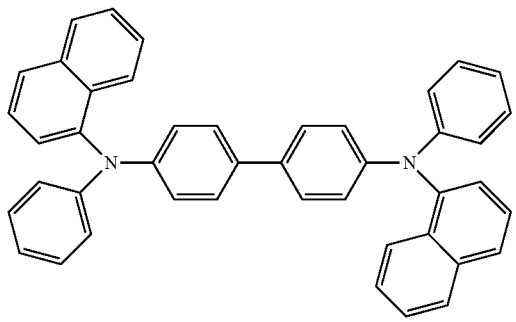
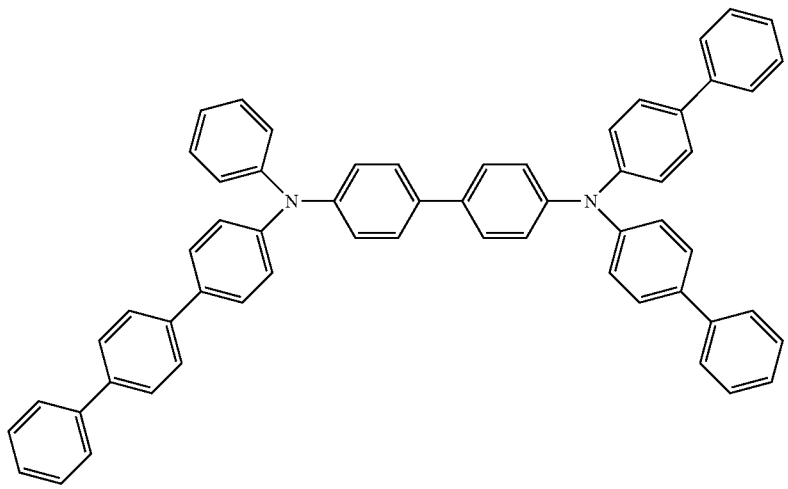
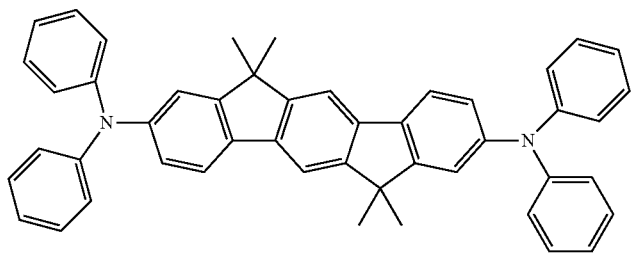

-continued
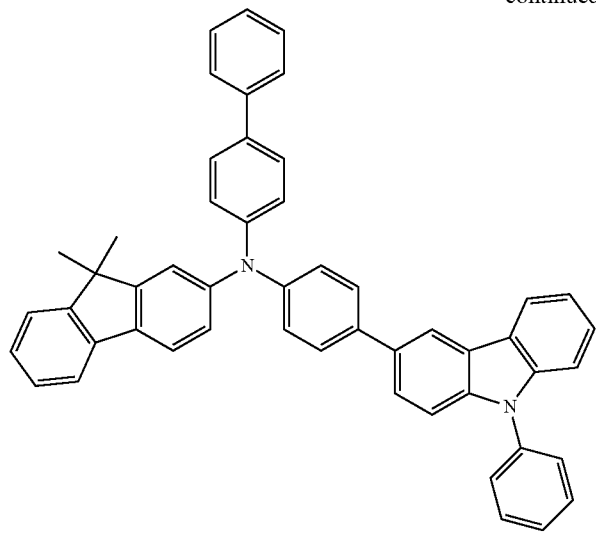
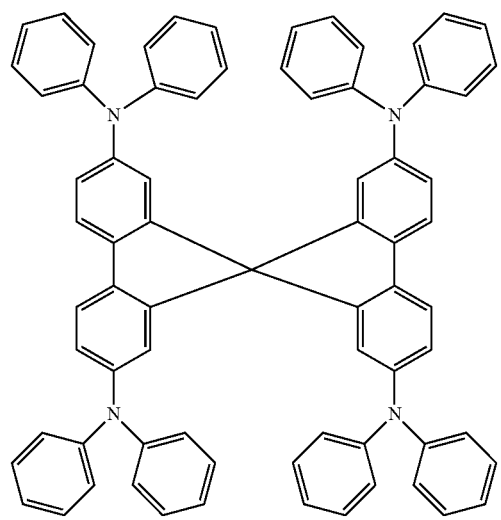
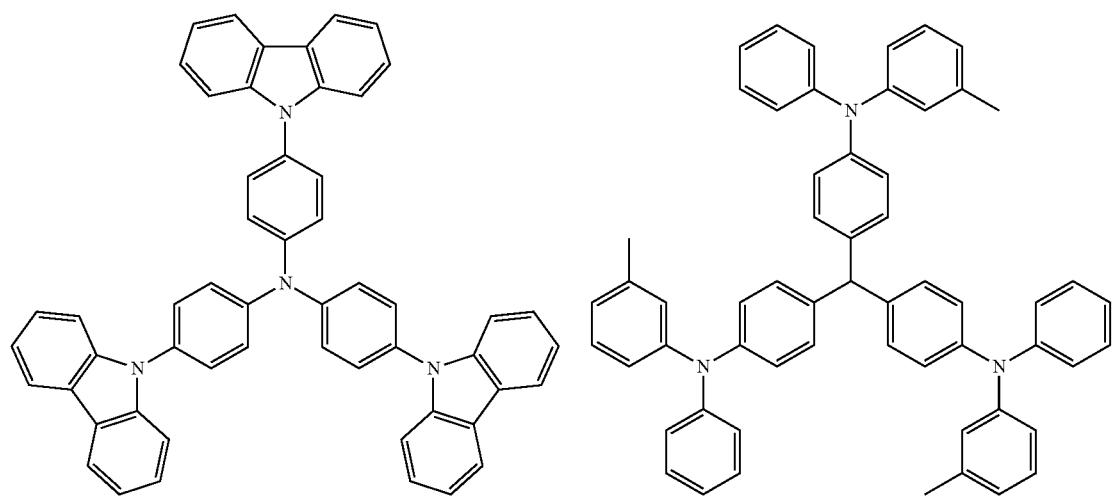
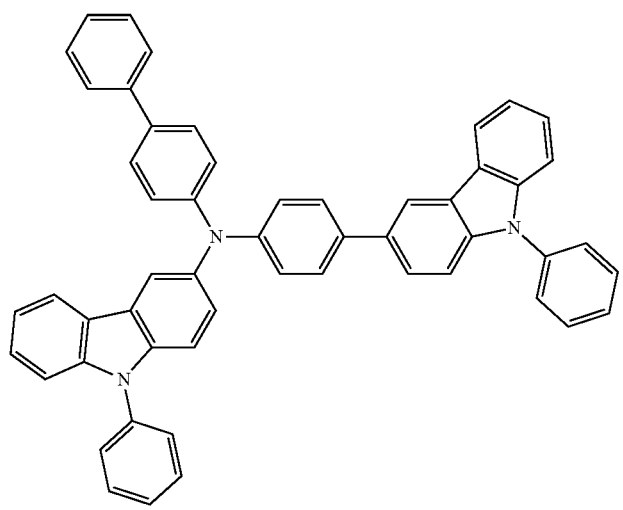

2. EIM/ETM/HBM

The EIM/ETM used in the compounds of the present disclosure is also sometimes referred to as an n-type organic semiconductor material. In principle, examples of suitable ETM materials are not particularly limited. Any metal complex or organic compound may be used as ETM as long as they can transfer electrons. Preferred organic ETM materials may be selected from the group consisting of tris (8-quinolinolato) aluminum, phenazine, phenanthroline, anthracene, phenanthrene, fluorene, bifluorene, spiro-bifluorene, phenylene-vinylene, triazine, triazole, imidazole, pyrene, perylene, trans-indenofluorene, cis-indenonfluorene, dibenzol-indenofluorene, indenonaphthalene, benzanthracene and their derivatives.

The hole-blocking layer (HBL) in the present disclosure is typically used to block holes from adjacent functional layers, particularly light-emitting layers. In contrast to a light-emitting device without a barrier layer, the presence of HBL usually leads to an increase in luminous efficiency. The hole-blocking material (HBM) of the hole-blocking layer (HBL) requires a lower HOMO than the adjacent functional layer, such as the light-emitting layer. In a preferred embodiment, the HBM has a greater energy level of excited state than the adjacent light-emitting layer, such as a singlet or triplet, depending on the emitter. In another preferred embodiment, the HBM has an electron-transport function. Typically, EIM/ETM materials with deep HOMO levels may be used as HBM.

In another aspect, compounds that may be used as EIM/ETM/HBM may be molecules comprising at least one of the following groups:

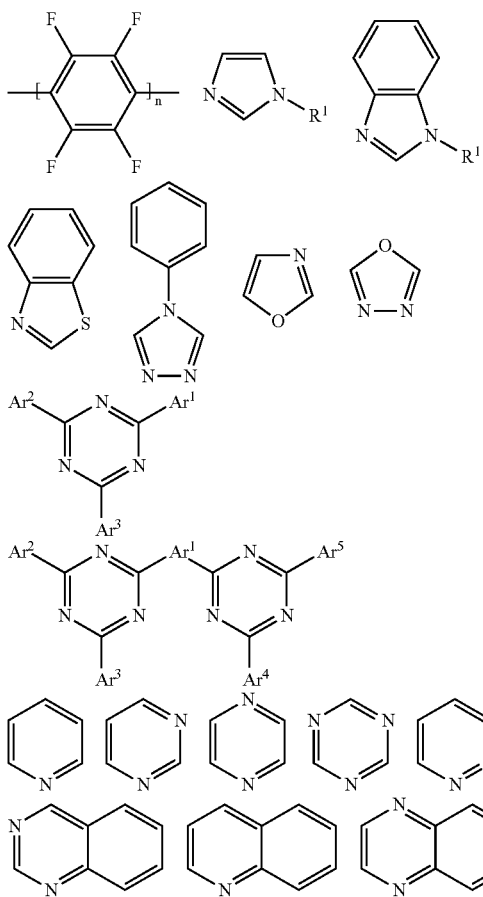

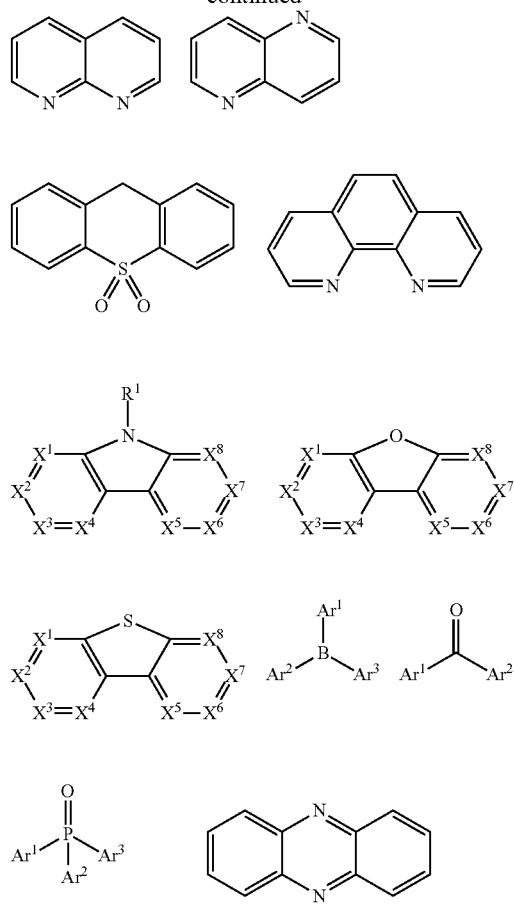

wherein $R^1$ may be selected from the group consisting of: hydrogen, alkyl, alkoxy, amino, alkene, alkyne, aralkyl, heteroalkyl, aryl and heteroaryl, wherein, when they are aryl or heteroaryl, they may have the same meaning as $Ar^1$ in HTM as described above; $Ar^1$-$Ar^5$ and $X^1$-$X^8$ may have the same meaning as $Ar^1$ in HTM as described above.

n may be an integer from 0 to 20.

On the other hand, examples of metal complexes that may be used as EIM/ETM may include, but are not limited to, the following general structure:

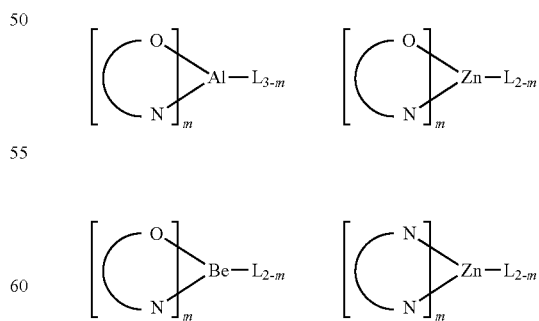

(O—N) or (N—N) is a bidentate ligand, wherein the metal coordinates with O, N, or N, N; L is an auxiliary ligand; and m is an integer whose value is from 1 to the maximum coordination number of the metal.

Non-limiting examples of suitable ETM compounds are listed in the following table:

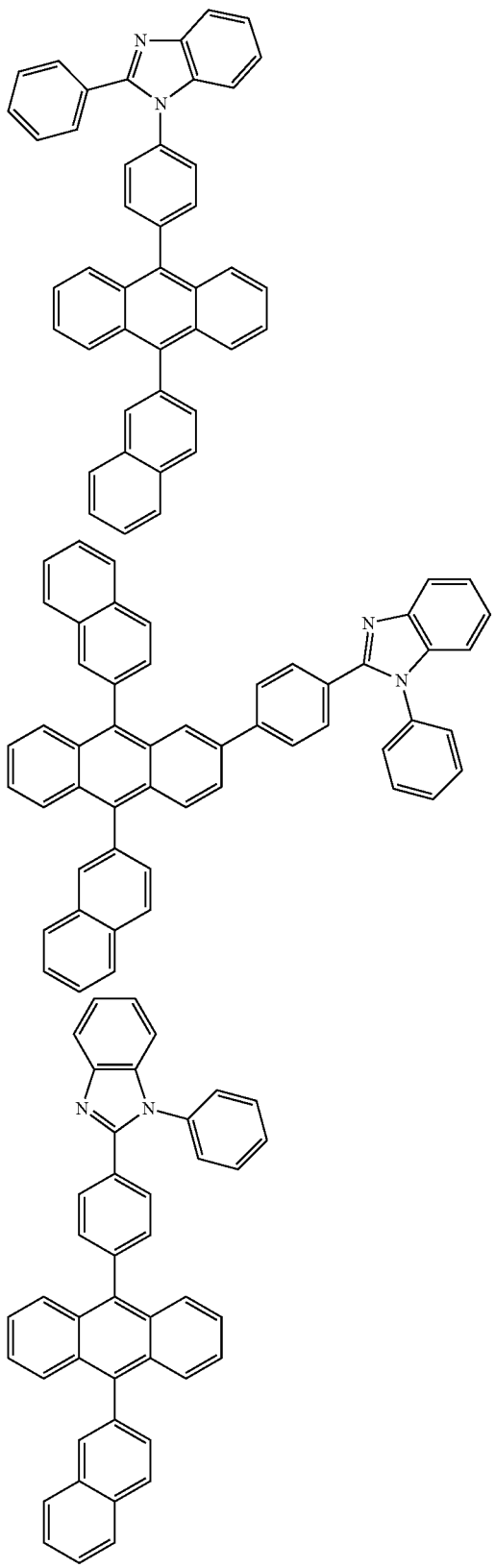

In another preferred embodiment, the organic alkali metal compound may be used as the EIM. In the present disclosure, the organic alkali metal compound may be understood as a compound having at least one alkali metal, i.e., lithium, sodium, potassium, rubidium, and cesium, and further comprising at least one organic ligand.

Non-limiting examples of suitable organic alkali metal compounds may include the compounds described in U.S. Pat. No. 7,767,317 B2, EP 1941562B1 and EP 1144543B1.

The preferred organic alkali metal compound may be a compound of the following formula:

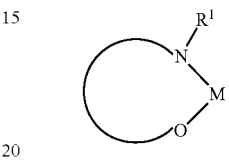

wherein $R^1$ has the same meaning as described above, and the arc represents two or three atoms and the bond to form a 5- or 6-membered ring with metal M when necessary, while the atoms may be optionally substituted with one or more $R^1$; and wherein M is an alkali metal selected from lithium, sodium, potassium, rubidium, and cesium.

The organic alkali metal compound may be in the form of a monomer, as described above, or in the form of an aggregate, for example, two alkali metal ions with two ligands, 4 alkali metal ions and 4 ligands, 6 alkali metal ions and 6 ligand, or in other forms.

The preferred organic alkali metal compound may be a compound of the following formula:

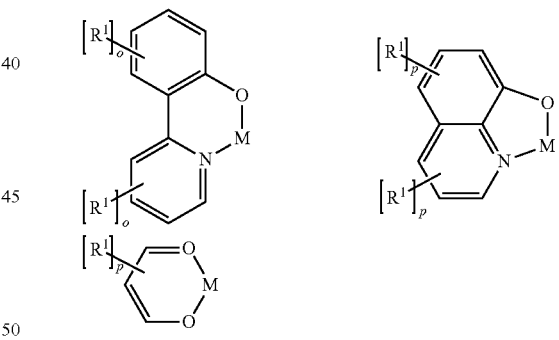

wherein, the symbols used are as defined above, and in addition: o, each time it may be the same or different, selected from 0, 1, 2, 3 or 4; and p, each time it may be the same or different, selected from 0, 1, 2 or 3. In a preferred embodiment, the alkali metal M is selected from the group consisting of lithium, sodium, potassium, more preferably lithium or sodium, and most preferably lithium.

In a preferred embodiment, the organic alkali metal compound may be injected into the electron-injection layer, and more preferably the electron-injection layer consists of the organic alkali metal compound.

In another preferred embodiment, the organic alkali metal compound is doped into other ETMs to form an electron-transport layer or an electron-injection layer, more preferably an electron-transport layer.

Non-limiting examples of a suitable organic alkali metal compound are listed in the following table:
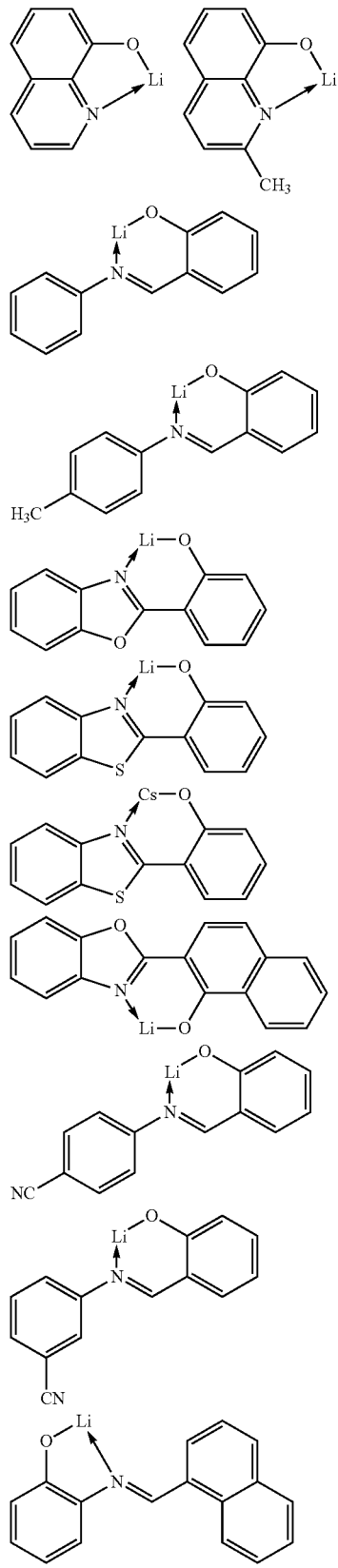
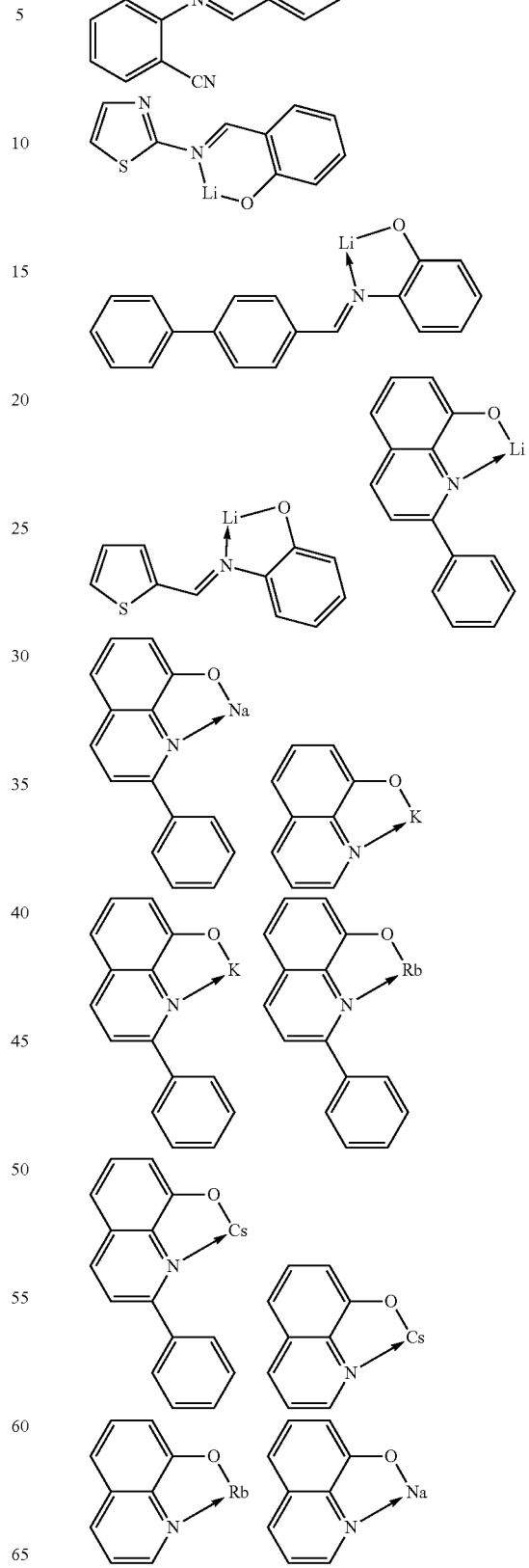

3. Triplet Host Materials:

Examples of triplet host material are not particularly limited and any metal complex or organic compound may be used as the host material as long as its triplet energy is greater than that of the light emitter, especially a triplet emitter or phosphorescent emitter.

Examples of metal complexes that may be used as triplet hosts may include, but are not limited to, the general structure as follows:

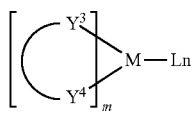

wherein M may be a metal; (Y³-Y⁴) may be a bidentate ligand, $Y^3$ and $Y^4$ may be independently selected from C, N, O, P, and S; L may be an auxiliary ligand; m may be an integer with the value from 1 to the maximum coordination number of the metal; and, m+n is the maximum number of coordination of the metal.

In a preferred embodiment, the metal complex which may be used as the triplet host has the following form:

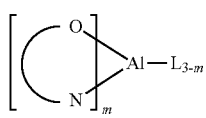 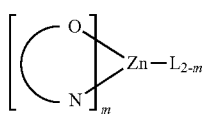

(O—N) may be a bidentate ligand in which the metal is coordinated to O and N atoms. In one embodiment, M may be selected from Ir and Pt.

Non-limiting examples of organic compounds are selected from: compounds comprising cyclic aryl groups, such as benzene, biphenyl, triphenyl, benzo, and fluorene; compounds comprising heterocyclic aryl groups, such as triphenylamine, dibenzothiophene, dibenzofuran, dibenzoselenophen, furan, thiophene, benzofuran, benzothiophene, benzoselenophene, carbazole, indolocarbazole, indolopyridine, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, or a combination thereof; and groups comprising 2 to 10 ring structures, which may be the same or different types of cyclic aryl or heterocyclic aryl and are linked to each other directly or by at least one of the following groups, such as oxygen atom, nitrogen atom, sulfur atom, silicon atom, phosphorus atom, boron atom, chain structure unit, and aliphatic ring, wherein each Ar may be further optionally substituted and the substituents may be any one of hydrogen, alkyl, alkoxy, amino, alkene, alkyne, aralkyl, heteroalkyl, aryl and heteroaryl, or a combination thereof.

The triplet host material may have hole and/or electron transport properties. In a preferred embodiment, the triplet host material may be selected from compounds comprising at least one of the following groups:

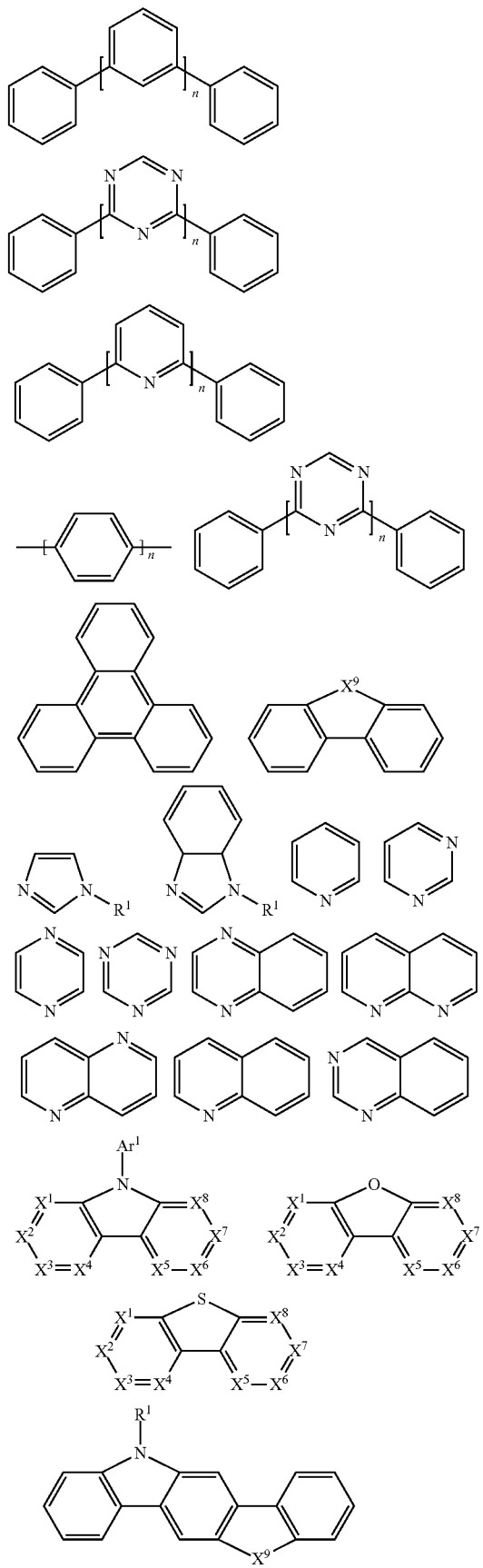

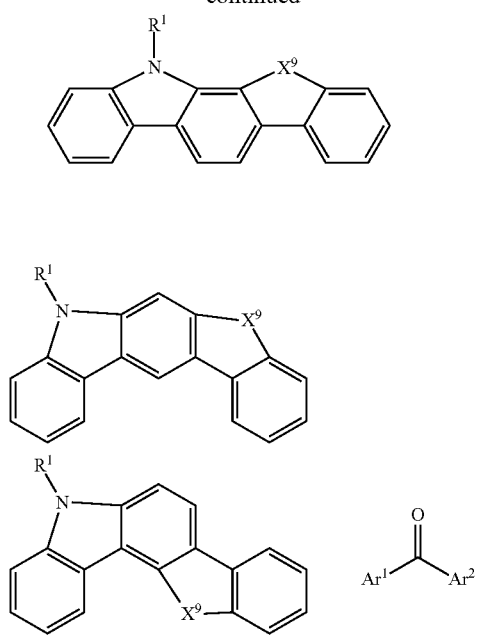

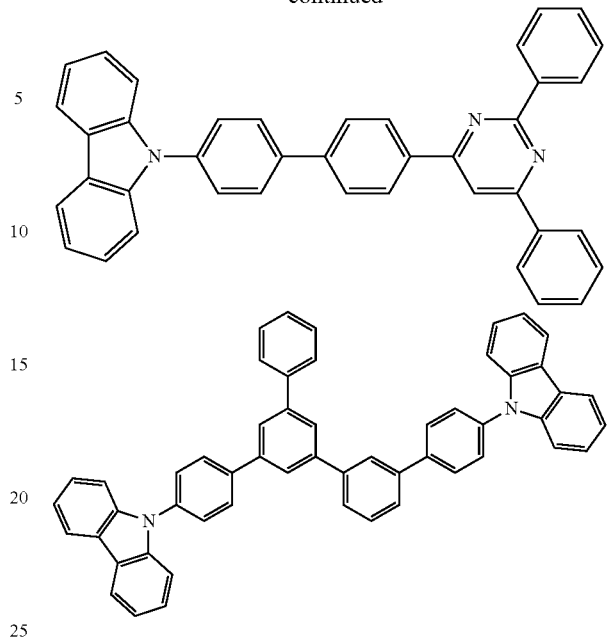

wherein R¹ may be independently selected from the group consisting of: hydrogen, alkyl, alkoxy, amino, alkene, alkyne, aralkyl, heteroalkyl, aryl and heteroaryl. And when the R¹ group is an aryl or a heteroaryl, it may has the same meaning as Ar¹ and Ar² as defined above with HTM. n can be an integer from 0 to 20, $X^1$-$X^8$ can be selected from CH or N, $X^9$ may be selected from $CR^1R^2$ or $NR^1$.

In a preferred embodiment, the mixture according to the disclosure comprises a triplet host material.

Non-limiting examples of suitable triplet host material are listed in the following table:

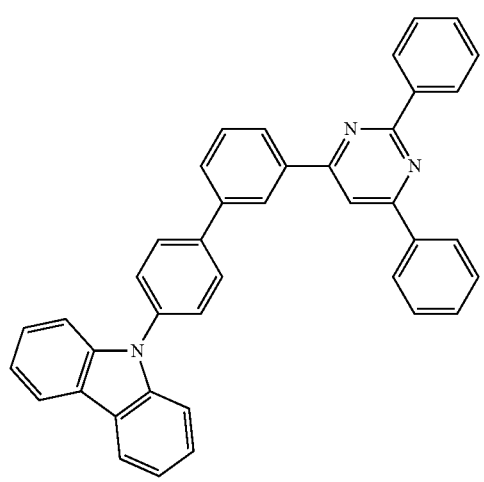

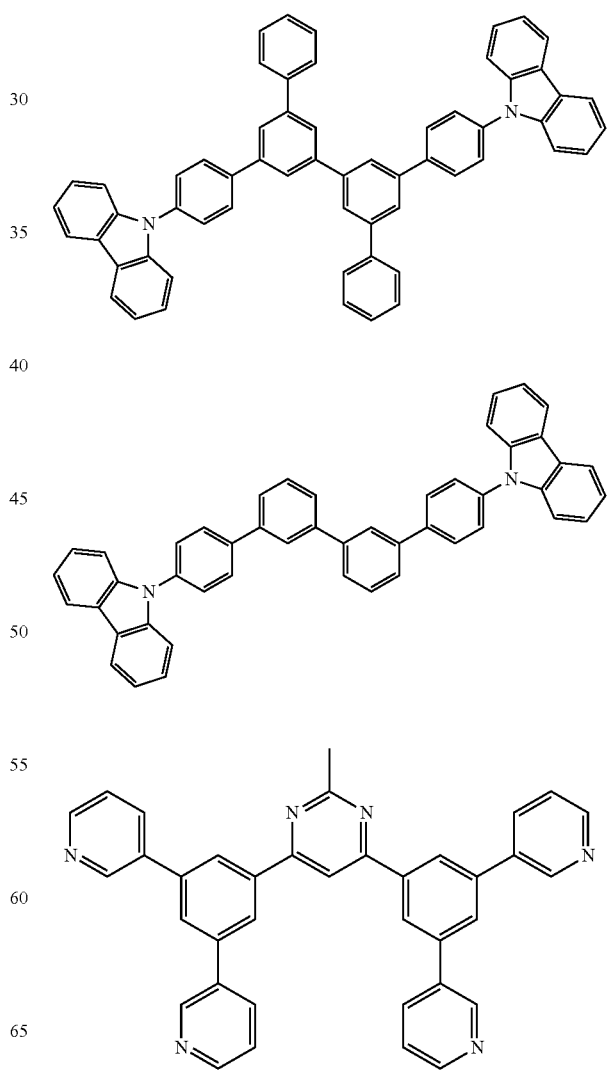

-continued

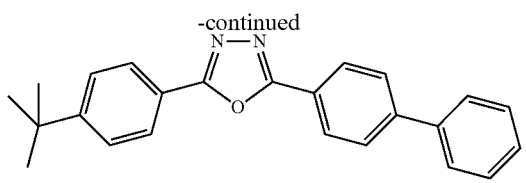

4. Singlet Host Material:

Examples of singlet host material are not particularly limited and any organic compound may be used as the host as long as its singlet state energy is greater than that of the light emitter, especially the singlet emitter or fluorescent light emitter.

Non-limiting examples of organic compounds used as singlet host materials may be selected from: cyclic aryl compounds, such as benzene, biphenyl, triphenyl, benzo, naphthalene, anthracene, phenalene, phenanthrene, fluorene, pyrene, chrysene, perylene, azulene; heterocyclic aryl compounds, such as triphenylamine, dibenzothiophene, dibenzofuran, dibenzoselenophen, furan, thiophene, benzofuran, benzothiophene, benzoselenophene, carbazole, indolocarbazole, indolopyridine, pyrrolodipyridine, pyrazole, imidazole, triazole, isoxazole, thiazole, oxadiazole, oxatriazole, dioxazole, thiadiazole, pyridine, pyridazine, pyrimidine, pyrazine, triazole, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and groups comprising 2 to 10 ring structures, which may be the same or different types of cyclic aryl or heterocyclic aryl and are linked to each other directly or by at least one of the following groups, such as oxygen atom, nitrogen atom, sulfur atom, silicon atom, phosphorus atom, boron atom, chain structure unit, and aliphatic rings.

In a preferred embodiment, the monomorphic host material may be selected from compounds comprising at least one of the following groups:

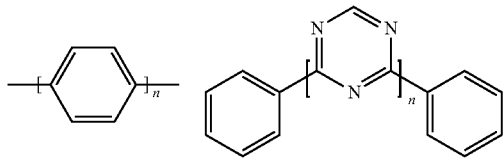

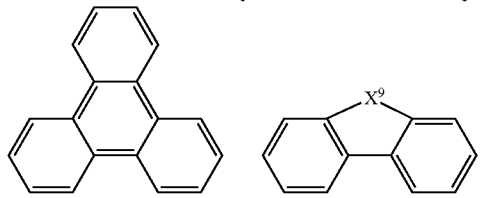

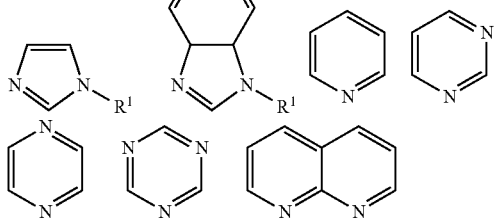

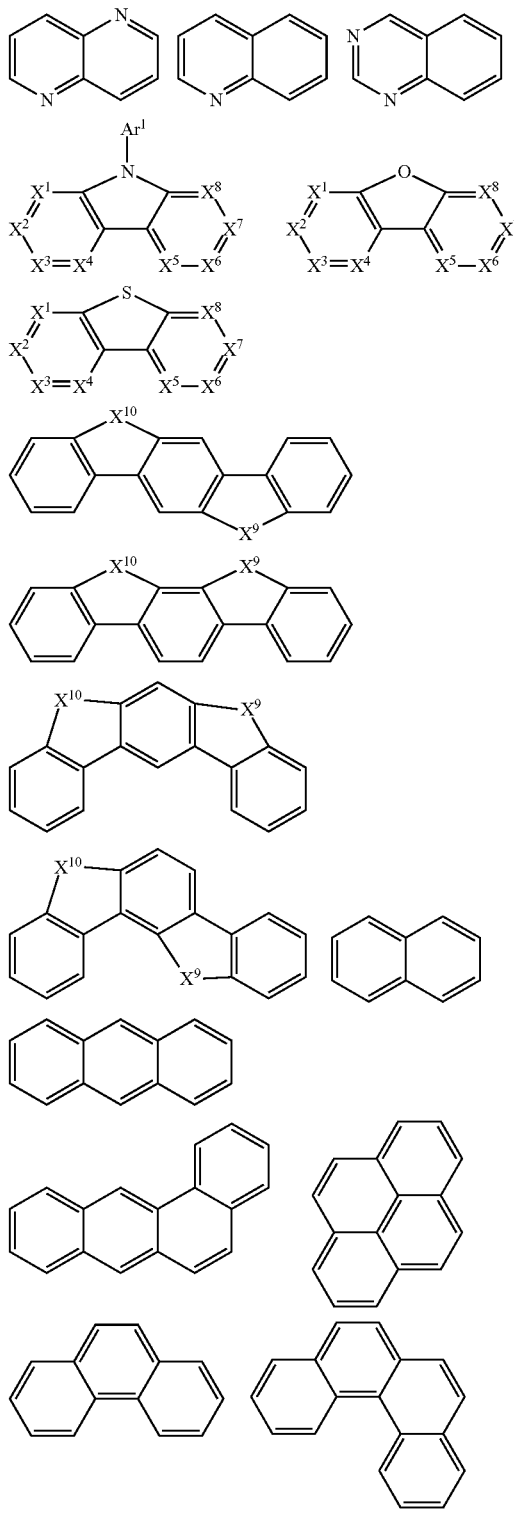

wherein $R^1$ may be independently selected from the group consisting of: hydrogen, alkyl, alkoxy, amino, alkene, alkyne, aralkyl, heteroalkyl, aryl and heteroaryl. And when the $R^1$ group is an aryl or a heteroaryl, it may has the same meaning as $Ar^1$ as defined above with HTM. n can be an integer from 0 to 20, $X^1$-$X^8$ can be selected from CH or N, $X^9$ and $X^{10}$ may be selected from $CR^1R^2$ or $NR^1$.

Non-limiting examples of a suitable anthryl singlet host material are listed in the following table:

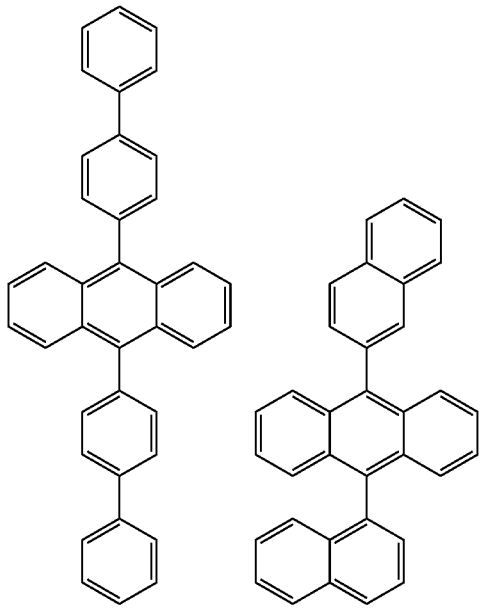

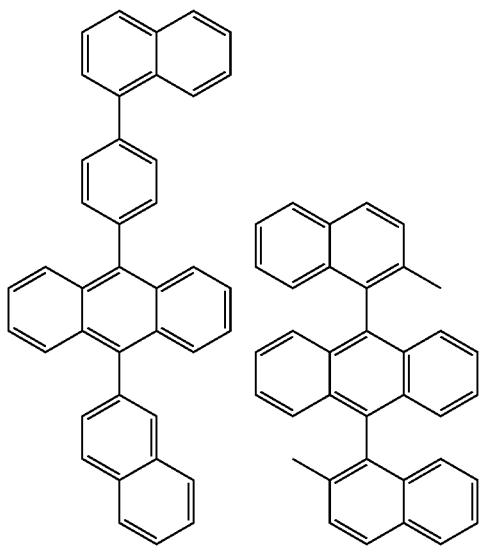

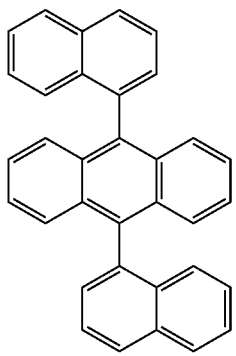

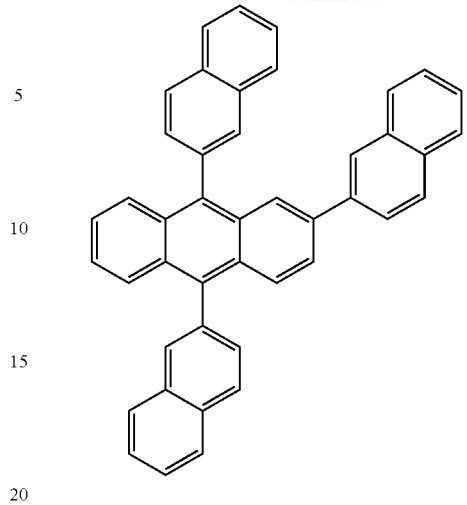

5. Hole-Blocking Material (HBM)

The hole-blocking layer (HBL) of the present disclosure is typically used to block holes from adjacent functional layers, particularly light-emitting layers. In contrast to a light-emitting device without a barrier layer, the presence of HBL usually leads to an increase in luminous efficiency. The hole-blocking material (HBM) of the hole-blocking layer (HBL) requires a lower HOMO than the adjacent functional layer, such as the light-emitting layer. In a preferred embodiment, the HBM has a greater energy level of excited state than the adjacent light-emitting layer, such as a singlet or triplet, depending on the emitter. In another preferred embodiment, the HBM has an electron-transport function. In one embodiment, the HBM used comprises the same molecules as the host material in the light-emitting layer. In another preferred embodiment, the HBM may be selected from compounds comprising at least one of the following groups:

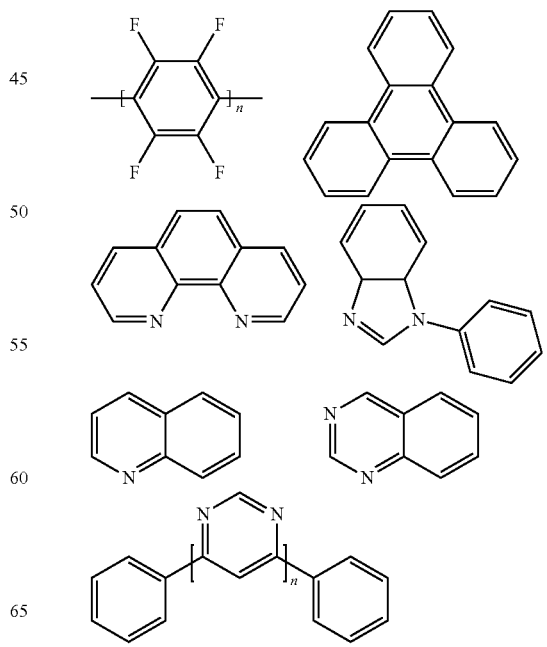

-continued

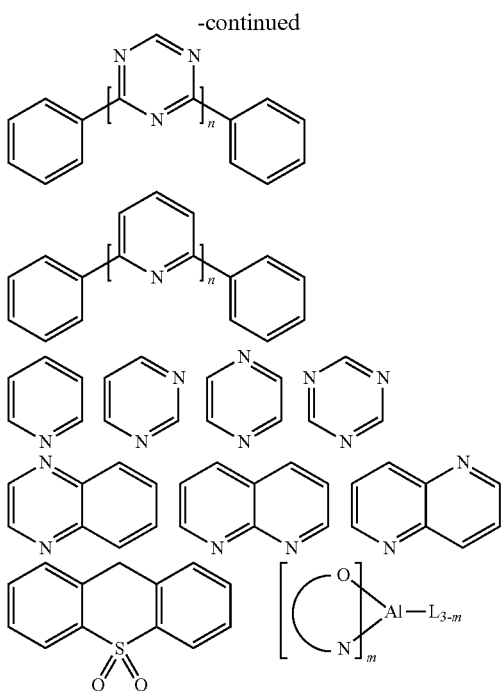

wherein n may be an integer from 0 to 20; L may be an auxiliary ligand; and m may be an integer from 1 to 3.

6. Singlet Emitter

Fluorescent emitter tends to have a longer conjugate π-electron system. To date, there have been many examples, such as, but not limited to, tyrylamine and its derivatives disclosed in JP2913116B and WO2001021729A1, and indenofluorene and its derivatives disclosed in WO2008/006449 and WO2007/140847.

In a preferred embodiment, the fluorescent emitter may be selected from the group consisting of monostyrylamines, distyrylamines, tristyrylamines, tetrastyrylamines, styrylphosphines, styryl ethers, and arylamines, or combinations thereof.

Mono styrylamine refers to a compound which comprises an unsubstituted or optionally substituted styryl group and at least one amine, most preferably an aryl amine. Distyrylamine refers to a compound comprising two unsubstituted or optionally substituted styryl groups and at least one amine, most preferably an aryl amine. Ternarystyrylamine refers to a compound which comprises three unsubstituted or optionally substituted styryl groups and at least one amine, most preferably an aryl amine. Quaternarystyrylamine refers to a compound comprising four unsubstituted or optionally substituted styryl groups and at least one amine, most preferably an aryl amine. Preferred styrene is stilbene, which may be further optionally substituted. The corresponding phosphines and ethers are defined similarly to amines. Aryl amine or aryl amine refers to a compound comprising three unsubstituted or optionally substituted cyclic or heterocyclic aryl systems directly attached to nitrogen. At least one of these cyclic or heterocyclic aryl systems is preferably selected from fused ring systems and most preferably has at least 14 aryl ring atoms. Among the preferred examples are aryl anthramine, aryl anthradiamine, aryl pyrene amines, aryl pyrene diamines, aryl chrysene amines and aryl chrysene diamine. Aryl anthramine refers to a compound in which a diarylamino group is directly attached to anthracene, most preferably at position 9. Aryl anthradiamine refers to a compound in which two diarylamino groups are directly attached to anthracene, most preferably at positions 9, 10. Aryl pyrene amines, aryl pyrene diamines, aryl chrysene amines and aryl chrysene diamine are similarly defined, wherein the diarylarylamino group is most preferably attached to position 1 or 1 and 6 of pyrene.

Non-limiting examples of fluorescent emitter based on vinylamine and arylamine are also preferred examples which may be found in the following patent documents: WO 2006/000388, WO 2006/058737, WO 2006/000389, WO 2007/065549, WO 2007/115610, U.S. Pat. No. 7,250,532 B2, DE 102005058557 A1, CN 1583691 A, JP 08053397 A, U.S. Pat. No. 6,251,531 B1, US 2006/210830 A, EP 1957606 A1, and US 2008/0113101 A1.

Non-limiting examples of fluorescent emitters based on distyrylbenzene and its derivatives may be found in, for example, U.S. Pat. No. 5,121,029.

Further preferred fluorescent emitters may be selected from the group consisting of: indenofluorene-amine and indenofluorene-diamine as disclosed in WO 2006/122630, benzoindenofluorene-amine and benzoindenofluorene-diamine as disclosed in WO 2008/006449, dibenzoindenofluorene-amine and dibenzoindenofluorene-diamine as disclosed in WO2007/140847.

Other materials useful as fluorescent emitter include polycyclic aryl compounds, especially any one selected from the derivatives of the following compounds: anthracenes such as 9,10-di-naphthylanthracene, naphthalene, tetraphenyl, phenanthrene, perylene such as 2,5,8,11-tetra-t-butylatedylene, indenoperylene, phenylenes such as 4,4'-(bis (9-ethyl-3-carbazovinylene)-1,1'-biphenyl, periflanthene, decacyclene, coronene, fluorene, spirobifluorene, arylpyren (e.g., US20060222886), arylenevinylene (e.g., U.S. Pat. Nos. 5,121,029, 5,130,603), cyclopentadiene such as tetraphenylcyclopentadiene, rubrene, coumarine, rhodamine, quinacridone, pyrane such as 4 (dicyanoethylene)-6-(4-dimethylaminostyryl-2-methyl)-4H-pyrane (DCM), thiapyran, bis (azinyl) imine-boron compounds (US 2007/0092753 A1), bis (azinyl) methene compounds, carbostyryl compounds, oxazone, benzoxazole, benzothiazole, benzimidazole, and diketopyrrolopyrrole, or combinations thereof. Non-limiting examples of some singlet emitter material may be found in the following patent documents: US 20070252517 A1, U.S. Pat. Nos. 4,769,292, 6,020,078, US 2007/0252517 A1, and US 2007/0252517 A1.

Non-limiting examples of fluorescent emitters are listed in the following table:

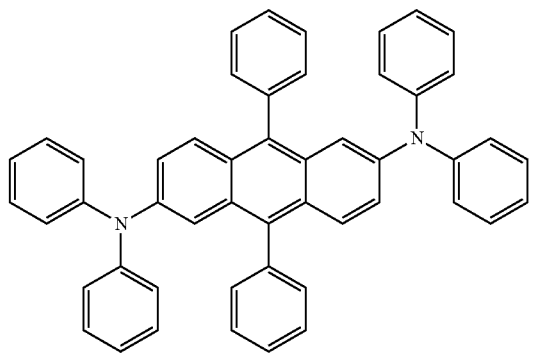

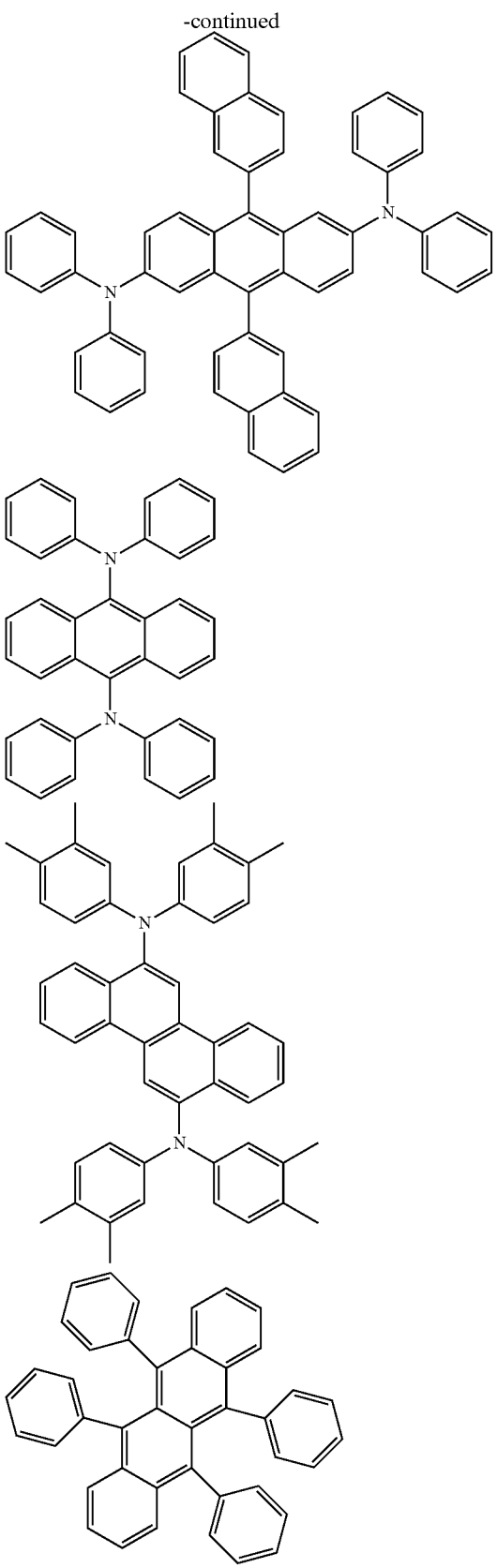

7. Triplet Emitter

The triplet emitter used in the present disclosure is also called a phosphorescent emitter. In a preferred embodiment, the triplet emitter may be a metal complex of the general formula M (L) n, wherein M may be a metal atom; L may be a same or different ligand each time it is present, and may be bonded or coordinated to the metal atom M at one or more positions; n may be an integer greater than 1, preferably 1, 2, 3, 4, 5 or 6. Alternatively, these metal complexes may be attached to a polymer by one or more positions, most preferably through an organic ligand.

In a preferred embodiment, the metal atom M may be selected from the group consisting of transition metal elements or lanthanides or actinides, preferably Ir, Pt, Pd, Au, Rh, Ru, Os, Sm, Eu, Gd, Tb, Dy, Re, Cu or Ag, and particularly preferably Os, Ir, Ru, Rh, Re, Pd, or Pt.

Preferably, the triplet emitter comprises a chelating ligand, i.e., a ligand, coordinated to the metal by at least two bonding sites, and it is particularly preferred that the triplet emitter comprises two or three identical or different bidentate or multidentate ligand. Chelating ligands help to improve stability of metal complexes.

Non-limiting examples of organic ligands may be selected from the group consisting of phenylpyridine derivatives, 7,8-benzoquinoline derivatives, 2 (2-thienyl) pyridine derivatives, 2 (1-naphthyl) pyridine derivatives, or 2 phenylquinoline derivatives. All of these organic ligands may be optionally substituted, for example, optionally substituted with fluoromethyl or trifluoromethyl. The auxiliary ligand may be preferably selected from acetylacetonate or picric acid.

In a preferred embodiment, the metal complex which may be used as the triplet emitter may have the following form:

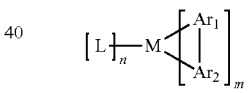

wherein M may be a metal selected from the group consisting of transition metal elements or lanthanides or actinides; $Ar^1$ may be the same or different cyclic group each time it is present, which comprises at least one donor atom, that is, an atom with a lone pair of electrons, such as nitrogen atom or phosphorus atom, which is coordinated to the metal through its ring group; $Ar^2$ may be the same or different cyclic group comprising at least one C atom and is coordinated to the metal through its ring group; $Ar^1$ and $Ar^2$ are covalently bonded together, wherein each of them may carry one or more substituents which may also be joined together by substituents; L may be the same or different at each occurrence and is an auxiliary ligand, preferably a bidentate chelating ligand, and most preferably a monoanionic bidentate chelating ligand; m is 1, 2 or 3, preferably 2 or 3, and particularly preferably 3; and, N is 0, 1, or 2, preferably 0 or 1, particularly preferably 0.

Non-limiting examples of triplet emitter materials that are extremely useful may be found in the following patent documents and references: WO 200070655, WO 200141512, WO 200202714, WO 200215645, EP 1191613, EP 1191612, EP 1191614, WO 2005033244, WO 2005019373, US 2005/0258742, WO 2009146770, WO 2010015307, WO 2010031485, WO 2010054731, WO 2010054728, WO 2010086089, WO 2010099852, WO 2010102709, US 20070087219 A1, US 20090061681 A1, US 20010053462 A1, Baldo, Thompson et al. Nature 403, (2000), 750-753, US 20090061681 A1, US 20090061681 A1, Adachi et al. Appl. Phys. Lett. 78 (2001), 1622-1624, J. Kido et al. Appl. Phys. Lett. 65 (1994), 2124, Kido et al. Chem. Lett. 657, 1990, US 2007/0252517 A1, Johnson et al., JACS 105, 1983, 1795, Wrighton, JACS 96, 1974, 998, Ma et al., Synth. Metals 94, 1998, 245, U.S. Pat. Nos. 6,824,895, 7,029,766, 6,835,469, 6,830,828, US 20010053462 A1, WO 2007095118 A1, US 2012004407A1, WO 2012007088A1, WO2012007087A1, WO 2012007086A1, US 2008027220A1, WO 2011157339A1, CN 102282150A, WO 2009118087A1.

The present disclosure further relates to a formulation which may comprise an organic compound as described above and at least one organic solvent. Examples of the organic solvents include, but are not limited to, methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxahexane, acetone, methyl ethyl ketone, 1,2-dichloroethane, 3-phenoxytoluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, naphthane, indene and/or their mixtures.

In a preferred embodiment, the formulation according to one aspect of the disclosure is a solution.

In another preferred embodiment, the formulation according to one aspect of the disclosure is a suspension.

The formulation in the examples of the present disclosure may comprise from 0.01 to 20 wt % of an organic compound according to an aspect of the present disclosure or the mixture thereof, more preferably from 0.1 to 15 wt %, more preferably from 0.2 to 10 wt %, and most preferably from 0.25 to 5 wt %.

The present disclosure also provides the use of said formulation as a coating or printing ink in the preparation of organic electronic devices, and particularly preferably by means of printing or coating in a preparation process.

Among them, suitable printing or coating techniques may include, but are not limited to, ink-jet printing, nozzle printing, typography, screen printing, dip coating, spin coating, blade coating, roll printing, torsion printing, lithography, flexography, rotary printing, brush coating or pad printing, slit type extrusion coating, and so on. Preferred are inkjet printing, screen printing and slit type extrusion coating. The solution or suspension may additionally comprise one or more components such as surface active compounds, lubricants, wetting agents, dispersing agents, hydrophobic agents, binders, etc., for adjusting viscosity, film forming properties, improving adhesion, and the like. For more information about printing techniques and their requirements for solutions, such as solvent, concentration, viscosity, etc., see Handbook of Print Media: Technologies and Production Methods, edited by Helmut Kipphan, ISBN 3-540-67326-1.

Based on the above polymers, the present disclosure also provides use of the organic compounds as described above in an organic electronic device, which may be selected from, but not limited to, organic light emitting diodes (OLED), organic photovoltaics (OPVs), organic light emitting electrochemical cells (OLEEC), organic field effect transistor (OFET), organic light emitting field effectors, organic lasers, organic spintronic devices, organic sensors, and organic plasmon emitting diodes, especially OLED. In the embodiment of the present disclosure, the organic compounds are preferably used in a light-emitting layer.

The present disclosure further provides an organic electronic device which may comprise at least one polymer as described above. Typically, such an organic electronic device may comprise at least a cathode, an anode, and a functional layer between the cathode and the anode, wherein the functional layer may comprise at least one of the polymers as described above.

The above-described luminescent device, especially OLED, may include a substrate, an anode, at least one light-emitting layer, and a cathode.

The substrate may be opaque or transparent. Transparent substrates may be used to make transparent light-emitting components. See, for example, Bulovic et al., Nature 1996, 380, p 29, and Gu et al., Appl. Phys. Lett. 1996, 68, p 2606. The substrate may be rigid or flexible. The substrate may be plastic, metal, semiconductor wafer or glass. Most preferably the substrate has a smooth surface. Substrates free of surface defects are particularly desirable. In a preferred embodiment, the substrate is flexible and may be selected from polymer films or plastic, with a glass transition temperature (Tg) of 150° C. or above, more preferably above 200° C., more preferably above 250° C., and most preferably above 300° C. Non-limiting examples of suitable flexible substrates are poly (ethylene terephthalate) (PET) and polyethylene glycol (2,6-naphthalene) (PEN).

The anode may comprise a conductive metal or a metal oxide, or a conductive polymer. The anode may easily inject holes into the hole-injection layer (HIL) or the hole-transport layer (HTL) or the light-emitting layer. In one embodiment, the absolute value of the difference between the work function of the anode and the HOMO energy level or the valence band energy level of the emitter in the light-emitting layer or of the p-type semiconductor material of the HIL or HTL or the electron-blocking layer (EBL) may be smaller than 0.5 eV, more preferably smaller than 0.3 eV, and most preferably smaller than 0.2 eV. Non-limiting examples of anode materials may include, but are not limited to, Al, Cu, Au, Ag, Mg, Fe, Co, Ni, Mn, Pd, Pt, ITO, aluminum-doped zinc oxide (AZO), and the like. Other suitable anode materials are known and may be readily selected for use by one of ordinary skill in the art. The anode material may be deposited using any suitable technique, such as suitable physical vapor deposition, including RF magnetron sputtering, vacuum thermal evaporation, electron beam (e-beam), and the like. In some embodiments, the anode may be patterned. The patterned ITO conductive substrate is commercially available and may be used to fabricate the device according to the disclosure.

The cathode may comprise a conductive metal or a metal oxide. The cathode may easily inject electrons into the EIL or ETL or directly into the light-emitting layer. In one embodiment, the absolute value of the difference between the work function of the cathode and the LUMO energy level or the valence band energy level of the emitter in the light-emitting layer or of the n-type semiconductor material of the electron-injection layer (EIL) or the electron-transport layer (ETL) or the hole-blocking layer (HBL) may be smaller than 0.5 eV, more preferably smaller than 0.3 eV, and most preferably smaller than 0.2 eV. In principle, all of the material that may be used as the cathode of an OLED may serve as a cathode material for the device of the present disclosure. Examples of the cathode material may include, but are not limited to, any one of Al, Au, Ag, Ca, Ba, Mg, LiF/Al, MgAg alloys, BaF2/Al, Cu, Fe, Co, Ni, Mn, Pd, Pt, ITO, or a combination thereof. The cathode material may be deposited using any suitable technique, such as suitable physical vapor deposition, including RF magnetron sputtering, vacuum thermal evaporation, electron beam (e-beam), and the like.

OLEDs may also comprise other functional layers such as hole-injection layer (HIL), hole-transport layer (HTL), electron-blocking layer (EBL), electron-injection layer (EIL), electron-transport layer (ETL), and hole-blocking layer (HBL), or a combination thereof. Materials suitable for use in these functional layers are described in detail above and in WO2010135519A1, US20090134784A1, and WO2011110277A1.

In a preferred embodiment, in the light emitting device according to the present disclosure, the light-emitting layer thereof may comprise the organic compound according to the present disclosure.

The light emitting device according to the present disclosure may have a light emission wavelength between 300 and 1000 nm, more preferably between 350 and 900 nm, and more preferably between 400 and 800 nm.

The present disclosure also provides the use of the organic electronic devices according to the present disclosure in a variety of electronic devices, including, but not limited to, display devices, lighting devices, light sources, sensors, and the like.

The present disclosure also provides electronic apparatus comprising the organic electronic devices according to the present disclosure, including, but not limited to, display devices, lighting devices, light sources, sensors, and the like.

The disclosure will now be described with reference to the preferred embodiments, but the disclosure is not to be construed as being limited to the following examples. It is to be understood that the appended claims are intended to cover the scope of the disclosure. Those skilled in the art will understand that modifications can be made to various embodiments of the disclosure with the teaching of the present disclosure, which will be covered by the spirit and scope of the claims of the disclosure.

Example 1

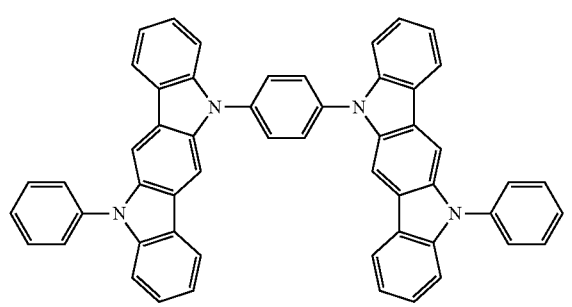

(1)

4,4'-bis (5-phenyl-11-indole [3,2-b] carbazolyl) benzene 2.6 g (10 mmol) of indolo [3,2-b] carbazole, 1.6 g (10 mmol) of bromobenzene, 6.9 g (50 mmol) of potassium carbonate, 0.26 g (1 mmol) of 18-crown ether-6, 0.3 g (1.5 mmol) of cuprous iodide and 100 ml of o-dichlorobenzene were added to a 50 ml three-necked flask in a $N_2$ atmosphere, and reacted at 140° C. TLC was used to follow the reaction process until the reaction was completed and dropped to room temperature. The reaction solution was poured into water, washed to remove $K_2CO_3$, and then sunction filtered to obtain a solid product. The product was washed with dichloromethane and recrystallized from ethanol to give 3 g of the product 5-phenylindole [3,2-b] carbazole.

1.6 g of the intermediate product obtained in the above procedure and 5.4 mmol of 5-phenylindole [3,2-b] carbazole was added to a 50 ml three-necked flask, while 0.65 g (2.5 mmol) of 1,4-dibromobenzene, 3.5 g (25 mmol) of potassium carbonate, 0.13 g (0.5 mmol) of 18-crown ether-6, 0.15 g (0.75 mmol) of cuprous iodide and 100 ml of o-dichlorobenzene were reacted in a $N_2$ atmosphere at 170° C. for 48 hours. TLC was used to follow the reaction process until the reaction was completed and dropped to room temperature. o-dichlorobenzene was removed by distillation under reduced pressure to give the crude product. The crude product was dissolved in 150 ml of methylene chloride and washed with water three times. The organic phase was combined, dried over anhydrous magnesium sulfate, evaporated to remove the dichloromethane solvent. The product was recrystallized from dichloromethane and methanol to give 2.5 g of a pale yellow solid. MS (APCI)=739.1.

Example 2

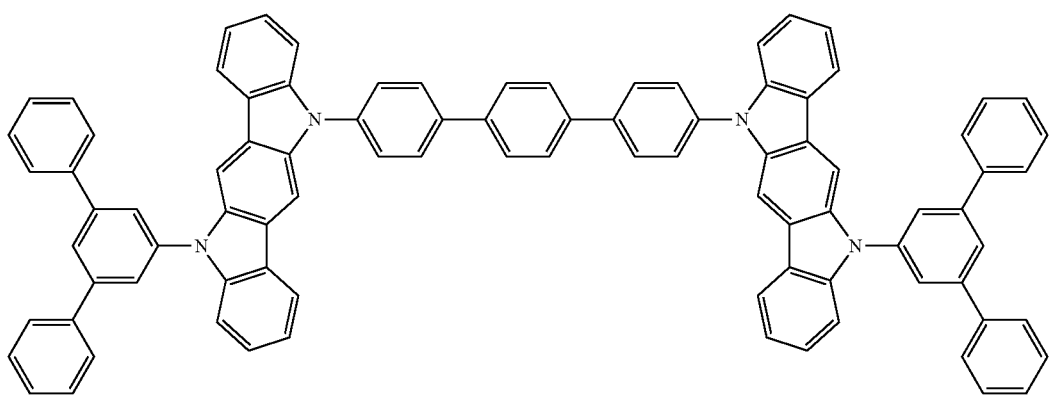

(2)

4,5'-bis (5-(3,5-diphenylbenzene)-11-H-indole [3,2-b] carbazolyl) terphenyl 2.6 g (10 mmol) of indolo [3,2-b] carbazole, 3.1 g (10 mmol) of diphenyl bromobenzene, 6.9 g (50 mmol) of potassium carbonate, 0.26 g (1 mmol) of 18-crown ether-6, 0.3 g (1.5 mmol) of cuprous iodide and 100 ml of o-dichlorobenzene were added to a 50 ml three-necked flask in a $N_2$ atmosphere, and reacted at 140° C. TLC was used to follow the reaction process until the reaction was completed and dropped to room temperature. The reaction solution was poured into water, washed to remove $K_2CO_3$, and then sunction filtered to obtain a solid product. The product was washed with dichloromethane and recrystallized from ethanol to give 4 g of the product 5-phenylindole [3,2-b] carbazole.

2.0 g of the intermediate product obtained in the above procedure and 5.4 mmol of 3,5-diphenyl phenylindole [3,2-b] carbazole was added to a 50 ml three-necked flask, while 0.89 g (2.5 mmol) of 4-bromo 4'-iodobiphenyl, 3.5 g (25 mmol) of potassium carbonate, 0.13 g (0.5 mmol) of 18-crown ether-6, 0.15 g (0.75 mmol) of cuprous iodide and 100 ml of o-dichlorobenzene were reacted in a $N_2$ atmosphere at 170° C. for 48 hours. TLC was used to follow the reaction process until the reaction was completed and dropped to room temperature. o-dichlorobenzene was removed by distillation under reduced pressure to give the crude product. The crude product was dissolved in 150 ml of methylene chloride and washed with water three times. The organic phase was combined, dried over anhydrous magnesium sulfate, evaporated to remove the dichloromethane solvent. The product was recrystallized from dichloromethane and methanol to give 2.5 g of a pale yellow solid. MS(APCI)=1195.5.

Example 3

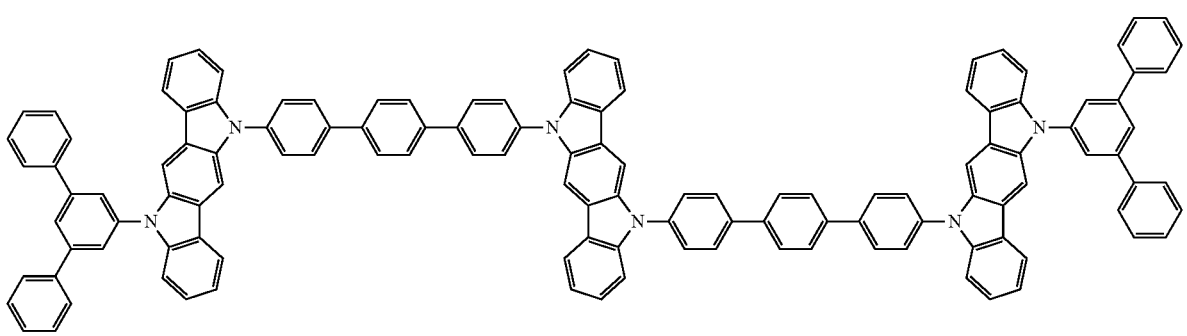

(3)

5,11-bis (4"-((5-(3,5-diphenylphenyl) indole [3,2-b] carbidinyl)-11-terphenyl) indole [3,2-b] carbazole In the present example, the synthesis step of the intermediate product 5-(3,5-diphenylbenzene)-11-H-indole [3,2-b] carbazolyl was the same as that in Example 2.

The procedure for the synthesis of another intermediate product used in this example, 5,11-bis (4"-bromodiphenyl) indole [3,2-b] carbazole, is as follows:

2.6 g (10 mmol) of indolo [3,2-b] carbazole, 8.7 g (20 mmol) of bromo-4"-iodobenzene, 6.9 g (50 mmol) of potassium carbonate, 0.26 g (1 mmol) of 18-crown ether-6, 0.3 g (1.5 mmol) of cuprous iodide and 100 ml of o-dichlorobenzene were added to a 50 ml three-necked flask in a $N_2$ atmosphere, and reacted at 140° C. TLC was used to follow the reaction process until the reaction was completed and dropped to room temperature. The reaction solution was poured into water, washed to remove $K_2CO_3$, and then sunction filtered to obtain a solid product. The product was washed with dichloromethane and recrystallized from ethanol to give 6 g of the product 5-phenylindole [3,2-b] carbazole.

4.0 g of the intermediate product obtained in the above procedure and 5.4 mmol of 5-(3,5-diphenyl phenyl) indole [3,2-b] carbazole was added to a 50 ml three-necked flask, while 4.4 g (5.0 mmol) of 5,11-bis (4"-brominated diphenyl) indole [3,2-b] carbazole, 3.5 g (25 mmol) of potassium carbonate, 0.13 g (0.5 mmol) of 18-crown ether-6, 0.15 g (0.75 mmol) of cuprous iodide and 100 ml of o-dichlorobenzene were reacted in a $N_2$ atmosphere at 170° C. for 48 hours. TLC was used to follow the reaction process until the reaction was completed and dropped to room temperature. o-dichlorobenzene was removed by distillation under reduced pressure to give the crude product. The crude product was dissolved in 150 ml of methylene chloride and washed with water three times. The organic phase was combined, dried over anhydrous magnesium sulfate, evaporated to remove the dichloromethane solvent. The product was recrystallized from dichloromethane and methanol to give 5 g of a pale yellow solid. The resulting product was dried in a vacuum oven. MS(APCI)=1678.1.

Example 4

Example 5

5-(2-(4', 6'-diphenyl-1', 3', 5'-triazinyl) phenyl-7-phenylindole [2,3-b] carbazole To a 250 ml one-necked flask 5 g (20 mmol) of indolo [3,2-b] carbazole, 3.1 g (20 mmol) of bromobenzene, 1.04 g (4 mmol) of 18-crown ether-6, 1.12 g (6 mmol) of CuI, 13.8 g (100 mmol) of potassium carbonate, and 300 ml of o-dichlorobenzene were added. Under the protection of nitrogen, reflux reaction was performed for 36 hours. TLC was used to follow the reaction process until the reaction was completed and dropped to room temperature. The reaction solution was poured into water, washed to remove $K_2CO_3$, and then sunction filtered to obtain a solid product. The product was washed with dichloromethane and recrystallized from ethanol to give 5 g of a pale yellow solid powder, 5-phenylindole [2,3-b] carbazole. MS (APCI)=333.4.

The above-obtained 3.3 g (10 mmol) of 5-phenylindole [2,3-b] carbazole, 4.0 g (10.5 mmol) of 2-(4', 6'-diphenyl-1', 3',5'-triazinyl) bromobenzene, 1.04 g (4 mmol) of 18-crown ether-6, 1.12 g (6 mmol) of CuI, 13.8 g (100 mmol) of potassium carbonate, and 300 ml of o-dichlorobenzene were

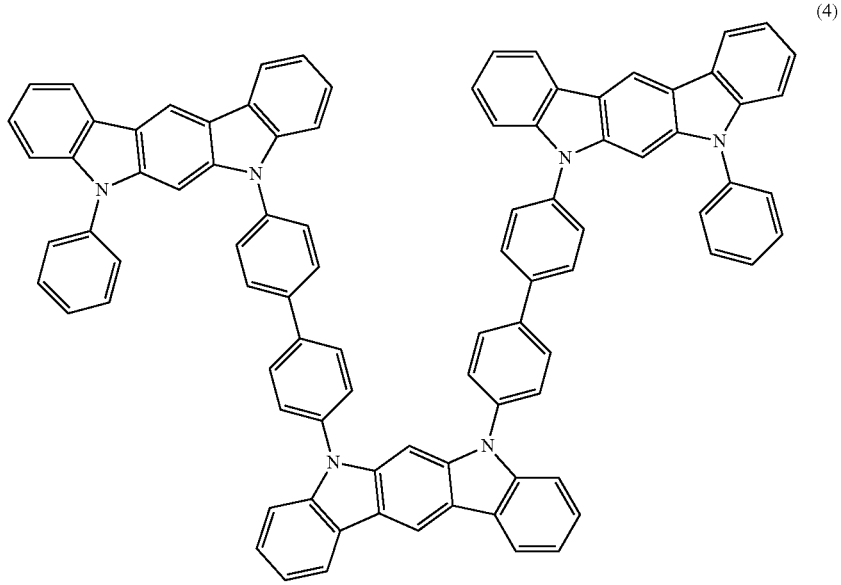 [SMILES: c1ccc(-n2c3ccccc3c3cc4c5ccccc5n(-c5ccc(-c6ccc(-n7c8ccccc8c8cc9c%10ccccc%10n(-c%10ccc(-c%11ccc(-n%12c%13ccccc%13c%13cc%14c%15ccccc%15n(-c%15ccccc%15)c%14cc%13%12)cc%11)cc%10)c9cc87)cc6)cc5)c4cc32)cc1]

(4)

5,7-bis (4'-((5-phenyl) indol [2,3-b] carbazol-yl)-7-biphenyl) indole [2,3-b] carbazole In the present example, the synthesis procedures of the intermediate products 5-phenylindole [2,3-b] carbazole and 5,7-bis (4'-bromodiphenyl) indole [2,3-b] carbazole were similar as those of the intermediate products 5-(3,5-diphenylbenzene) indole [3,2-b] carbazole and 5,11-bis (4"-bromo-triphenyl) indole [3,2-b] carbazole as described in Example 3. The reaction temperature and the reaction time used in the reaction process were the same. The last two intermediates formed the final product of 5,7-bis (4"-((5-phenyl) indole [2,3-b] carbazolyl)-7-biphenylyl) indole [2,3-b] carbazole (4) catalyzed by Cu (I) in a Ulman reaction. MS (APCI)=1221.5 added. Under the protection of nitrogen, reflux reaction was performed for 48 hours. TLC was used to follow the reaction process until the reaction was completed and dropped to room temperature. The reaction solution was poured into water, washed to remove $K_2CO_3$, and then sunction filtered to obtain a solid product. The product was washed with dichloromethane and recrystallized from ethanol and petroleum ether to give 4.5 g of a pale yellow solid powder. MS (APCI)=640.8.

The energy level of the organic material can be calculated by quantum computation, for example, using TD-DFT (time-dependent density functional theory) by Gaussian03W (Gaussian Inc.), the specific simulation methods of which can be found in WO2011141110. Firstly, the molecular geometry is optimized by semi-empirical method "Ground State/Semi-empirical/Default Spin/AM1" (Charge 0/Spin Singlet), and then the energy structure of organic molecules is calculated by TD-DFT (time-density functional theory) "TD-SCF/DFT/Default Spin/B3PW91" and the basis set "6-31G (d)" (Charge 0/Spin Singlet). The HOMO and LUMO levels are calculated using the following calibration formula, wherein $S_1$, $T_1$, and resonance factor $f(S_1)$ are used directly.

HOMO(eV)=((HOMO(G)×27.212)−0.9899)/1.1206

LUMO(eV)=((LUMO(G)×27.212)−2.0041)/1.385 wherein HOMO (G) and LUMO (G) are the direct calculation results of Gaussian 09W, in units of Hartree. The results are shown in Table 1:

TABLE 1

| Material | HOMO [eV] | LUMO [eV] | $f(S_1)$ | $T_1$ [eV] | $S_1$ [eV] | $\Delta_{ST}$ |
|---|---|---|---|---|---|---|
| (1) | −5.33 | −2.35 | 0.027 | 2.73 | 2.77 | 0.04 |
| (2) | −5.37 | −2.43 | 0.909 | 2.71 | 2.76 | 0.05 |
| (3) | −5.35 | −2.38 | 1.148 | 2.72 | 2.76 | 0.04 |
| (4) | −5.49 | −2.43 | 0.241 | 2.75 | 2.86 | 0.11 |
| (5) | −5.45 | −2.78 | 0.002 | 2.84 | 2.85 | 0.01 |

Meanwhile, the HOMO and LUMO electron cloud distributions of materials (1) to (5) are shown in FIG. 1

The HOMO and LUMO electron cloud distributions of materials (1) to (4) are overlapped as preferred, so that the corresponding material resonance factor f ($S_1$) is correspondingly higher.

The resonant factor f ($S_1$) is in a range of 0.001 and 1.5, and the fluorescence quantum luminescence efficiency of the materials can be preferably improved. And the value of $\Delta(S_1-T_1)$ is no higher than 0.11 eV, which satisfies the conditions of less than 0.25 eV for delayed fluorescent emission.

As a comparison with the above-mentioned fluorescent emitter materials, the delayed fluorescent emitter material of the D-A system is labeled with Ref 1:

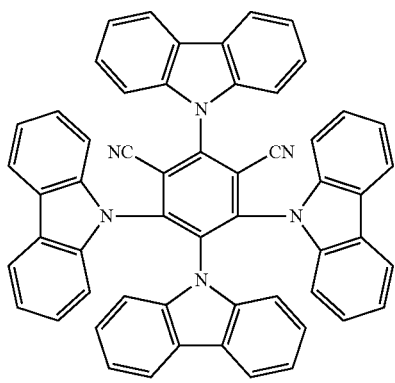

Ref 1

Preparation of OLED Devices:
The preparation steps of OLED devices with ITO/NPD (35 nm)/5%(1)~(5): mCP (15 nm)/TPBi (65 nm)/LiF (1 nm)/Al (150 nm)/cathode are as follows:
  a, cleaning of the conductive glass substrate: prior to first-time use, washing with the use of various solvents (such as one or more of chloroform, acetone or isopropyl alcohol) and then treating with UV and ozone;
  b. thermal deposition in high vacuum (1×10$^{-6}$ mbar) with HTL (35 nm), EML (15 nm), and ETL (65 nm);
  c, cathode: thermal deposition in high vacuum (1×10$^{-6}$ mbar) with LiF/Al (1 nm/150 nm);
  d, packaging: packaging the device in a nitrogen glove box with UV hardened resin.

The current-voltage (J-V) characteristics of each OLED device are characterized by characterization equipment, while important parameters such as efficiency, lifetime and external quantum efficiency were recorded. It was determined that the luminous efficiency and lifetime of OLED1 (corresponding to raw material (1)) were both 3 times or above of that of OLEDRef1 (corresponding to raw material (Ref1)). The OLED3 (corresponding to raw material (3)) had a luminous efficiency 4 times of and a lifttime 6 times of those of OLED Ref1. Particularly, the maximum external quantum efficiency of OLED3 was higher than 10%. It can be seen that the luminous efficiency and life of the OLED device prepared by using the organic mixture of the present disclosure is greatly improved.

It is to be understood that the application of the disclosure is not limited to the above-described examples and that those skilled in the art would understand that it may be modified or changed in accordance with the above description, all of which are within the scope of the claims appended hereto.

What is claimed is:
1. An organic compound having the following general structural formula (1):

General Structural Formula (1)

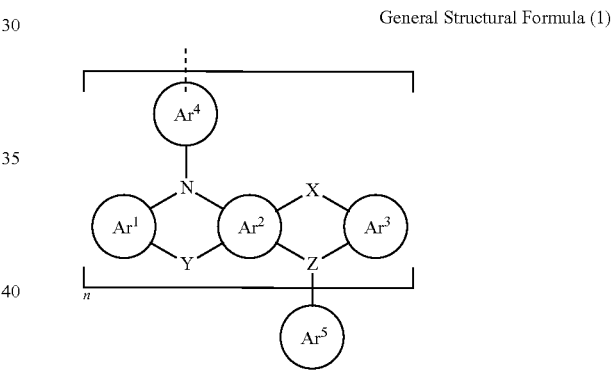

wherein the symbols and signs used therein have the following meanings:
  $Ar^1$, $Ar^2$, $Ar^3$, $Ar^4$ or $Ar^5$ is the same or different in multiple occurrences, independently selected from the group consisting of an aromatic, heteroaromatic or nonaromatic ring system having 2 to 20 carbon atoms, and is optionally substituted with one or more $R^1$ groups, wherein the $R^1$ group in multiple occurrences is the same as or different from each other;
  n is 3 or 4;
  X, Y in each occurrence are the same or different doubly-bridging groups, each of X, Y is connected to $Ar^2$ or $Ar^3$ by a single bond or a double bond and is selected from the group consisting of: a single bond, $N(R^1)$, $B(R^1)$, $C(R^1)_2$, O, C=O, C=S, C=Te, C=$NR^1$, $Si(R^1)_2$, C=C($R^1)_2$, S, S=O, $SO_2$, P=O, P=S, P=Se, P=Te, Se, Te, $P(R^1)$, and P(=O)$R^1$, or a combination of any two, three or four thereof;
  Z in each occurrence is the same or different triply-bridging group, wherein each Z is connected to $Ar^1$ or $Ar^2$ or $Ar^5$ by a single bond or a double bond;
  $R^1$ in each occurrence is the same or different and independently selected from the group consisting of —H, —F, —Cl, Br, I, -D, —CN, —NO$_2$, —CF$_3$, B(OR$_2$)$_2$, Si(R$_2$)$_3$, straight chain alkane, alkane ether, alkane sulfide having 1 to 10 carbon atoms, branched alkane, cycloalkane, alkane ether having 3 to 10 carbon atoms; R$^1$ is optionally substituted with one or more active groups R$^2$, and wherein one or more non-adjacent methylene groups of R$^1$ are optionally replaced by R$^2$C=CR$^2$, C=C, Si(R$^2$)$_2$, Ge(R$^2$)$_2$, Sn(R$^2$)$_2$, C=O, C=S, C=Se, C=N(R$^2$), O, S, —COO—, or CONR$^2$; one or more H atoms of R$^1$ are optionally replaced by D, Cl, Br, I, CN or N$_2$, or replaced by an aromatic amine group containing one or more reactive groups R$^2$ or aromatic group and optionally substituted with a heteroaromatic ring, or replaced by an optionally substituted or unsubstituted carbazole;

R$^2$ in each occurrence is the same or different and independently selected from H, D, aliphatic alkanes having 1 to 10 carbon atoms, aryl hydrocarbons, optionally substituted or unsubstituted aryl ring or heterocyclic aryl ring containing 5 to 10 carbon atoms;

at least one of X and Z is not identical to Y; and the dotted line in the general structural formula (1) represents one bond between adjacent monomers in the organic compound.

2. The organic compound according to claim 1, wherein Ar$^1$, Ar$^2$, Ar$^a$, Ar$^4$, or Ar$^5$ in multiple occurrences is the same or different and independently selected from the group consisting of aromatic ring or heteroaromatic ring having 2 to 20 carbon atoms.

3. The organic compound according to claim 1, wherein the triply-bridging group Z is selected from the group consisting of the following structural groups:

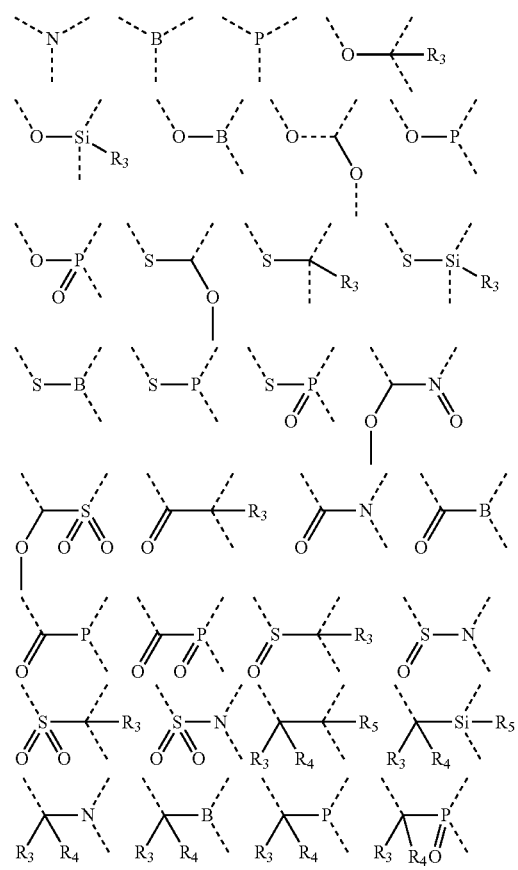

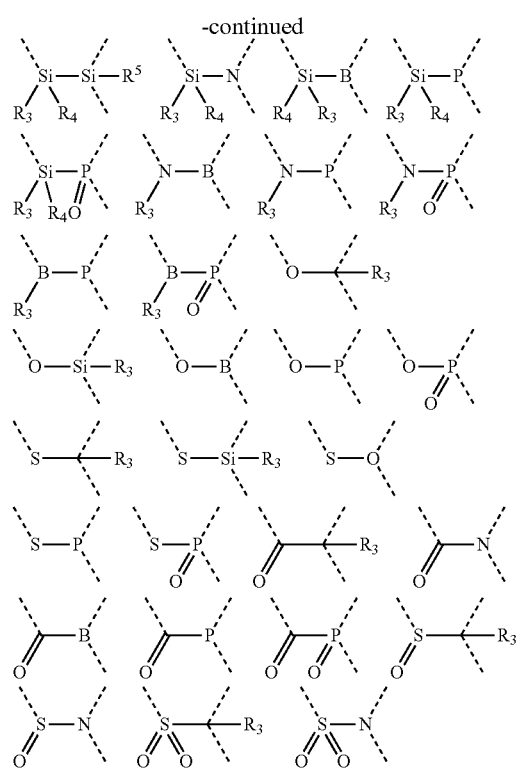

wherein the dotted line indicated by each of the above-mentioned groups represents a bond connected to the structural units Ar$^2$, Ar$^3$ or Ar$^5$.

4. The organic compound according to claim 1, wherein the organic compound has a structural formula selected from the following structural formulas (2), (3), (4), (5) and (6):

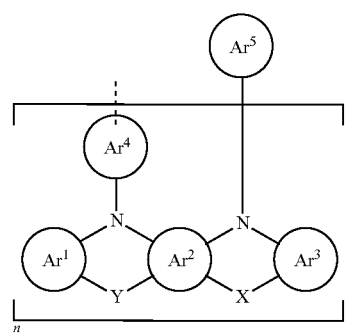

(2)

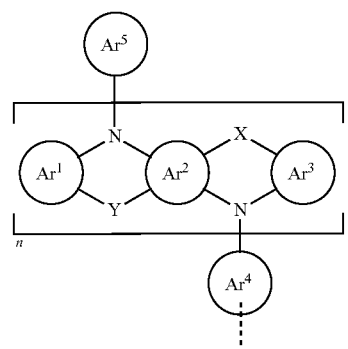

(3)

(4)

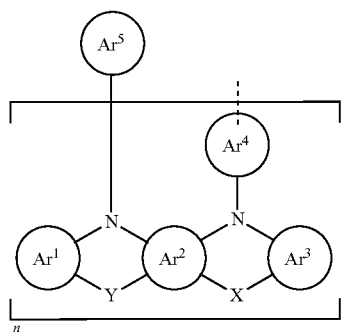

(5)

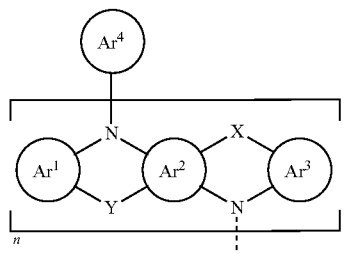

(6)

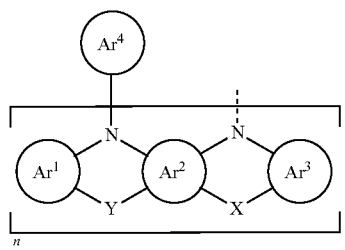

wherein, X or Y in each occurrence is the same or different bridging group and each independently selected from a single bond, N(R$^1$), B(R$^1$), C(R$^1$)$_2$, O, Si(R$^1$)$_2$, C=C(R$^1$)$_2$, S, S=O, SO$_2$, P(R$^1$) and P(=O) R$^1$, and wherein a dotted line represents a covalent bond for connection between two groups.

5. The organic compound according to claim 1, wherein Ar$^1$, Ar$^2$ or Ar$^3$ in multiple occurrences is the same or different and independently selected from:

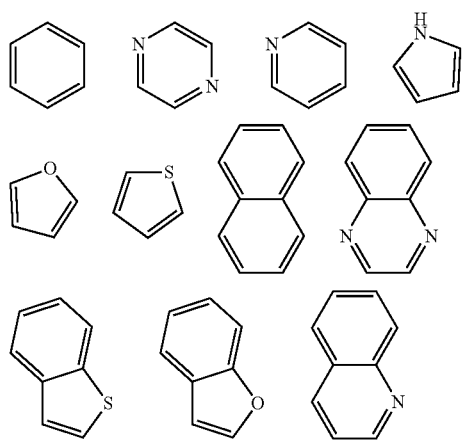

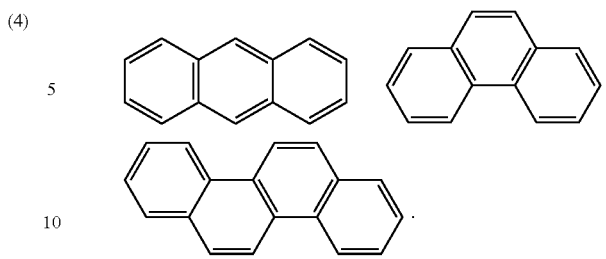

6. The organic compound according to claim 1, wherein the organic compound contains at least one structural unit selected from the group consisting of structures (2a), (3a), (4a), (5a) and (6a):

(2a)

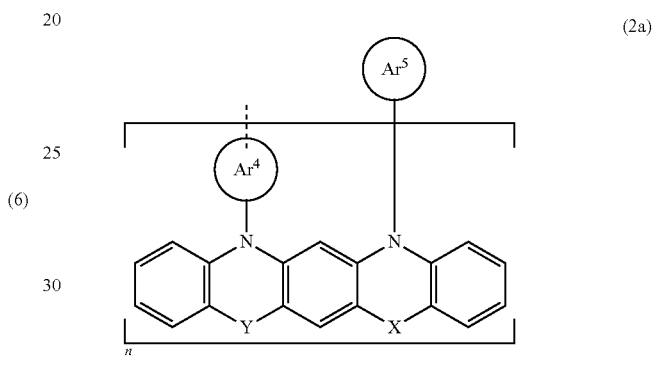

(3a)

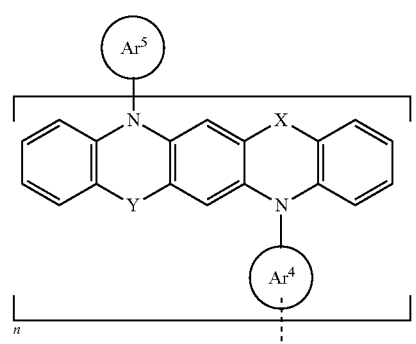

(4a)

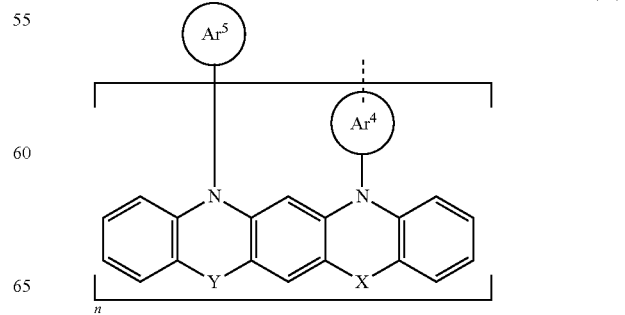

(5a)
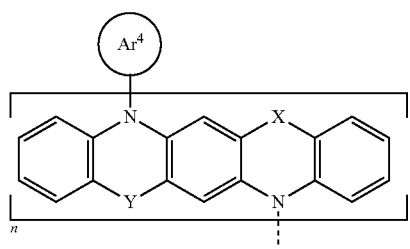
(6a)
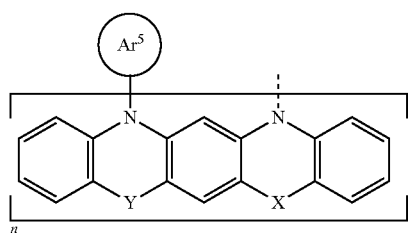
7. The organic compound according to claim 1, wherein Ar$^4$ or Ar$^5$, in multiple occurrences, is the same or different, and comprises a structural unit selected from the following or any combination thereof:
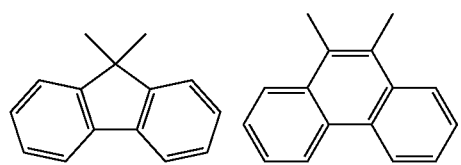
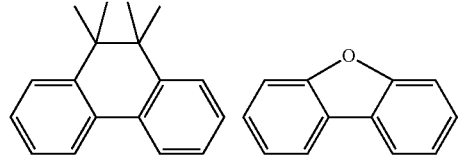
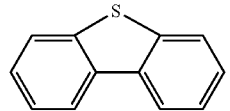
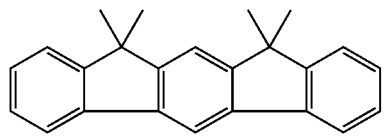
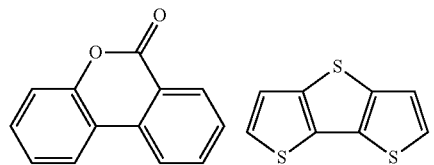
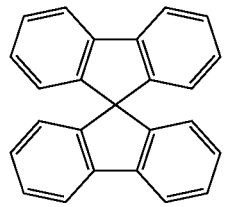 
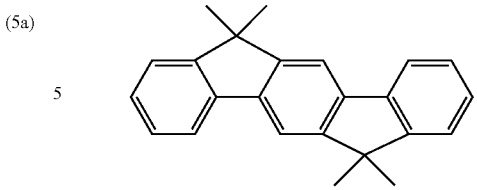
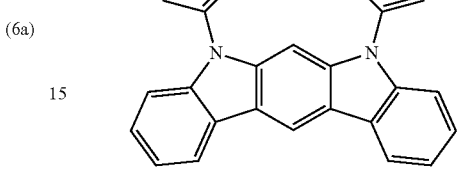
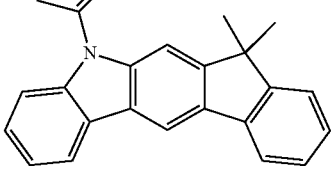
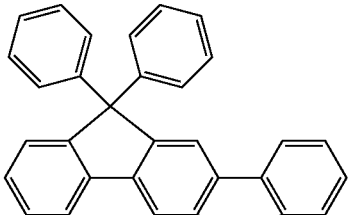
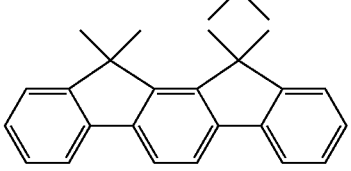
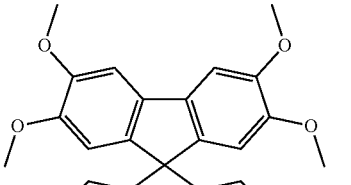
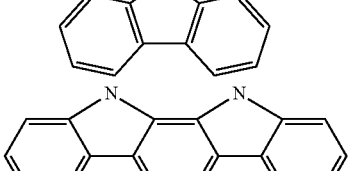
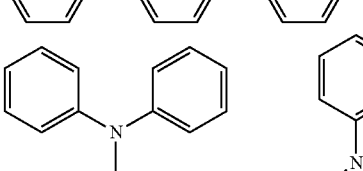
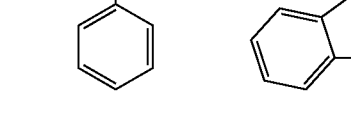

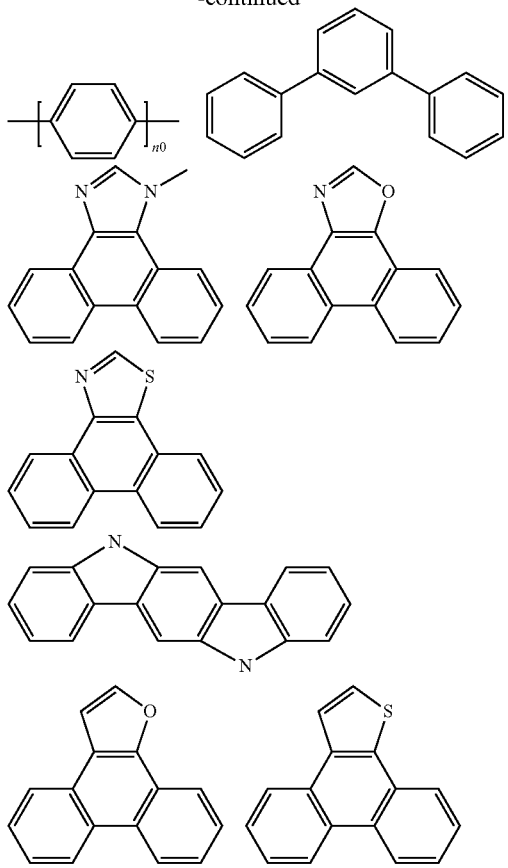

wherein $n_0$ is 1, 2, 3 or 4.

8. The organic compound according to claim 1, wherein the organic compound has a $(S_1-T_1) \leq 0.30$ eV, wherein the $(S_1-T_1)$ represents energy difference between the organic compound singlet $(S_1)$ and triplet $(T_1)$.

9. The organic compound according to claim 1, wherein, in multiple occurrences of $Ar^4$ and $Ar^5$, at least one of the $Ar^4$ and $Ar^5$ groups comprises an electron-donor group and/or at least one of the $Ar^4$ and $Ar^5$ groups comprises an electron-acceptor group.

10. The organic compound according to claim 9, wherein the electron-donor group is selected from the group consisting of:

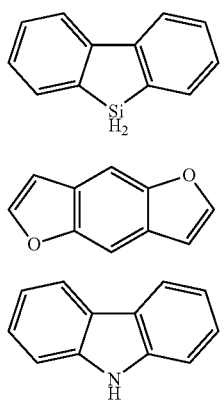

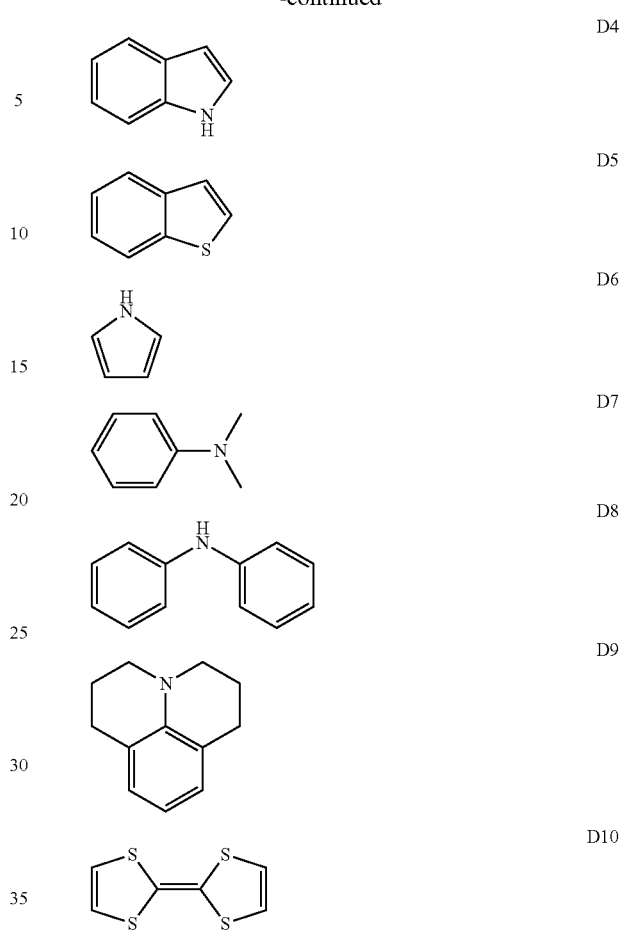

11. The organic compound according to claim 9, wherein the electron-acceptor group is selected from F, a cyano group, or a structural unit selected from structural units comprising any of the following groups:

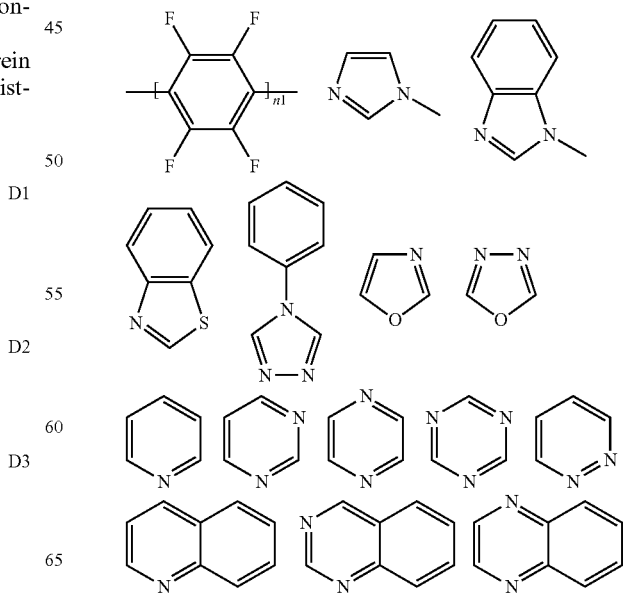

-continued

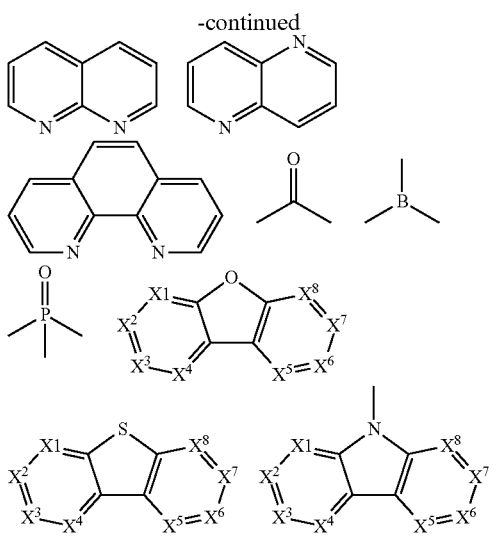

wherein $n_1$ is an integer selected from 1 to 3; $X^1$-$X^8$ is selected from $CR^1$ or N, and at least one of $X^1$-$X^8$ is N.

12. The organic compound according to claim 1, wherein the organic compound has a molecular weight of ≤4000 g/mol.

13. A mixture comprising an organic compound having the following general structural formula (1):

General Structural Formula (1)

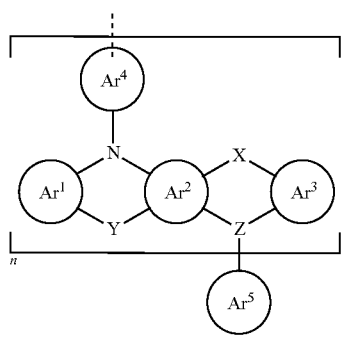

wherein the symbols and signs used therein have the following meanings:

Ar$^1$, Ar$^2$, Ar$^3$, Ar$^4$ or Ar$^5$ is the same or different in multiple occurrences, independently selected from the group consisting of an aromatic, heteroaromatic or nonaromatic ring system having 2 to 20 carbon atoms, and is optionally substituted with one or more R$^1$ groups, wherein the R$^1$ group in multiple occurrences is the same as or different from each other;

n is 3 or 4;

X, Y in each occurrence are the same or different doubly-bridging groups, each of X, Y is connected to Ar$^2$ or Ar$^3$ by a single bond or a double bond and is selected from the group consisting of: a single bond, N(R$^1$), B(R$^1$), C(R$^1$)$_2$, O, C=O, C=S, C=Te, C=NR$^1$, Si(R$^1$)$_2$, C=C(R$^1$)$_2$, S, S=O, SO$_2$, P=O, P=S, P=Se, P=Te, Se, Te, P(R$^1$), and P(=O)R$^1$, or a combination of any two, three or four thereof;

Z in each occurrence is the same or different triply-bridging group, wherein each Z is connected to Ar$^1$ or Ar$^2$ or Ar$^5$ by a single bond or a double bond;

R$^1$ in each occurrence is the same or different and independently selected from the group consisting of —H, —F, —Cl, Br, I, -D, —CN, —NO$_2$, —CF$_3$, B(OR$_2$)$_2$, Si(R$_2$)$_3$, straight chain alkane, alkane ether, alkane sulfide having 1 to 10 carbon atoms, branched alkane, cycloalkane, alkane ether having 3 to 10 carbon atoms; R$^1$ is optionally substituted with one or more active groups R$^2$, and wherein one or more non-adjacent methylene groups of R$^1$ are optionally replaced by R$^2$C=CR$^2$, C=C, Si(R$^2$)$_2$, Ge(R$^2$)$_2$, Sn(R$^2$)$_2$, C=O, C=S, C=Se, C=N(R$^2$), O, S, —COO—, or CONR$^2$; one or more H atoms of R$^1$ are optionally replaced by D, F, Cl, Br, I, CN or N$_2$, or replaced by an aromatic amine group containing one or more reactive groups R$^2$ or aromatic group and optionally substituted with a heteroaromatic ring, or replaced by an optionally substituted or unsubstituted carbazole;

R$^2$ in each occurrence is the same or different and independently selected from H, D, aliphatic alkanes having 1 to 10 carbon atoms, aryl hydrocarbons, optionally substituted or unsubstituted aryl ring or heterocyclic aryl ring containing 5 to 10 carbon atoms;

at least one of X and Z is not identical to Y; and the dotted line in the general structural formula (1) represents one bond between adjacent monomers in the organic compound, wherein the mixture further includes at least one further organic functional material selected from hole-injection material, hole-transport material, electron-transport material, electron-injection material, electron-blocking material, hole-blocking material, emitter, host material, or a combination thereof.

14. A formulation comprising an organic compound having the following general structural formula (1):

General Structural Formula (1)

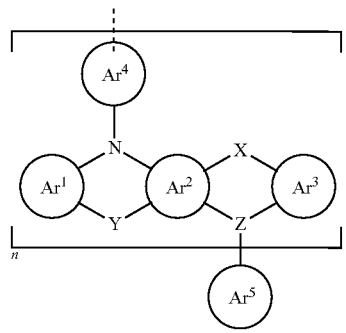

wherein the symbols and signs used therein have the following meanings:

Ar$^1$, Ar$^2$, Ar$^3$, Ar$^4$ or Ar$^5$ is the same or different in multiple occurrences, independently selected from the group consisting of an aromatic, heteroaromatic or nonaromatic ring system having 2 to 20 carbon atoms, and is optionally substituted with one or more R$^1$ groups, wherein the R$^1$ group in multiple occurrences is the same as or different from each other n is 3 or 4;

X, Y in each occurrence are the same or different doubly-bridging groups, each of X, Y is connected to Ar$^2$ or Ar$^3$ by a single bond or a double bond and is selected from the group consisting of: a single bond, N(R$^1$), B(R$^1$), C(R$^1$)$_2$, O, C=O, C=S, C=Te, C=NR$^1$, Si(R$^1$)$_2$, C=C(R$^1$)$_2$, S, S=O, SO$_2$, P=O, P=S, P=Se, P=Te, Se, Te, P(R$^1$), and P(=O)R$^1$, or a combination of any two, three or four thereof;

Z in each occurrence is the same or different triply-bridging group, wherein each Z is connected to Ar$^1$ or Ar$^2$ or Ar$^5$ by a single bond or a double bond;

R$^1$ in each occurrence is the same or different and independently selected from the group consisting of —H, —F, —Cl, Br, I, -D, —CN, —NO$_2$, —CF$_3$, B(OR$_2$)$_2$, Si(R$_2$)$_3$, straight chain alkane, alkane ether, alkane sulfide having 1 to 10 carbon atoms, branched alkane, cycloalkane, alkane ether having 3 to 10 carbon atoms; R$^1$ is optionally substituted with one or more active groups R$^2$, and wherein one or more non-adjacent methylene groups of R$^1$ are optionally replaced by R$^2$C=CR$^2$, C=C, Si(R$^2$)$_2$, Ge(R$^2$)$_2$, Sn(R$^2$)$_2$, C=O, C=S, C=Se, C=N(R$^2$), O, S, —COO—, or CONR$^2$; one or more H atoms of R$^1$ are optionally replaced by D, F, Cl, Br, I, CN or N$_2$, or replaced by an aromatic amine group containing one or more reactive groups R$^2$ or aromatic group and optionally substituted with a heteroaromatic ring, or replaced by an optionally substituted or unsubstituted carbazole;

R$^2$ in each occurrence is the same or different and independently selected from H, D, aliphatic alkanes having 1 to 10 carbon atoms, aryl hydrocarbons, optionally substituted or unsubstituted aryl ring or heterocyclic aryl ring containing 5 to 10 carbon atoms;

at least one of X and Z is not identical to Y; and the dotted line in the general structural formula (1) represents one bond between adjacent monomers in the organic compound, wherein the formulation further includes at least one organic solvent.

15. The formulation according to claim 14, wherein the formulation comprises the organic compound or a mixture comprising the organic compound and at least one further organic functional material selected from hole-injection material, hole-transport material, electron-transport material, electron-injection material, electron-blocking material, hole-blocking material, emitter, host material, or a combination thereof, and based on the weight of the formulation, the organic compound or the mixture comprising the organic compound is in an amount of 0.01 wt % to 20 wt %.

16. The organic compound according to claim 1, wherein the organic compound has a ($S_1$-$T_1$)≤0.25 eV, wherein the ($S_1$-$T_1$) represents energy difference between the organic compound singlet ($S_1$) and triplet ($T_1$).

17. The organic compound according to claim 1, wherein the organic compound has a ($S_1$-$T_1$)≤0.20 eV, wherein the ($S_1$-$T_1$) represents energy difference between the organic compound singlet ($S_1$) and triplet ($T_1$).

18. The organic compound according to claim 1, wherein the organic compound has a ($S_1$-$T_1$)≤0.10 eV, wherein the ($S_1$-$T_1$) represents energy difference between the organic compound singlet ($S_1$) and triplet ($T_1$).

19. The organic compound according to claim 1, wherein the organic compound has a molecular weight of ≤3000 g/mol.

20. The organic compound according to claim 1, wherein the organic compound has a molecular weight of ≤2500 g/mol.

21. The organic compound according to claim 1, wherein the organic compound has a molecular weight of ≤2000 g/mol.

22. The formulation according to claim 14, wherein the formulation comprises the organic compound or a mixture comprising the organic compound and at least one further organic functional material selected from hole-injection material, hole-transport material, electron-transport material, electron-injection material, electron-blocking material, hole-blocking material, emitter, host material, or a combination thereof, and based on the weight of the formulation, the organic compound or the mixture comprising the organic compound is in an amount of 0.1 wt % to 15 wt %.

23. The formulation according to claim 14, wherein the formulation comprises the organic compound or a mixture comprising the organic compound and at least one further organic functional material selected from hole-injection material, hole-transport material, electron-transport material, electron-injection material, electron-blocking material, hole-blocking material, emitter, host material, or a combination thereof, and based on the weight of the formulation, the organic compound or the mixture comprising the organic compound is in an amount of 0.2 wt % to 10 wt %.

24. The formulation according to claim 14, wherein the formulation comprises the organic compound or a mixture comprising the organic compound and at least one further organic functional material selected from hole-injection material, hole-transport material, electron-transport material, electron-injection material, electron-blocking material, hole-blocking material, emitter, host material, or a combination thereof, and based on the weight of the formulation, the organic compound or the mixture comprising the organic compound is in an amount of 0.25 wt % to 5 wt %.

* * * * *